(12) United States Patent
Staas et al.

(10) Patent No.: US 8,541,028 B2
(45) Date of Patent: Sep. 24, 2013

(54) METHODS FOR MANUFACTURING DELIVERY DEVICES AND DEVICES THEREOF

(75) Inventors: Jay K. Staas, Madison, AL (US); Thomas R. Tice, Indian Springs, AL (US); Bruce W. Hudson, Pleasant Grove, AL (US); Arthur J. Tipton, Birmingham, AL (US)

(73) Assignee: Evonik Corporation, Parsippany, NJ (US)

( * ) Notice: Subject to any disclaimer, the term of this patent is extended or adjusted under 35 U.S.C. 154(b) by 2045 days.

(21) Appl. No.: 11/196,591

(22) Filed: Aug. 3, 2005

(65) Prior Publication Data

US 2006/0029637 A1    Feb. 9, 2006

Related U.S. Application Data

(60) Provisional application No. 60/599,174, filed on Aug. 4, 2004.

(51) Int. Cl.
*A61K 9/14* (2006.01)

(52) U.S. Cl.
USPC .......................................... 424/484

(58) Field of Classification Search
None
See application file for complete search history.

(56) References Cited

U.S. PATENT DOCUMENTS

| | | | |
|---|---|---|---|
| 2,648,609 A | 8/1953 | Wurster, et al. | |
| 3,089,824 A | 5/1963 | Wurster et al. | |
| 3,117,027 A | 1/1964 | Lindlof, et al. | |
| 3,196,827 A | 7/1965 | Wurster et al. | |
| 3,207,824 A | 9/1965 | Wurster et al. | |
| 3,241,520 A | 3/1966 | Wurster et al. | |
| 3,253,944 A | 5/1966 | Wurster, et al. | |
| 3,773,919 A | 11/1973 | Boswell et al. | 424/19 |
| 3,978,203 A | 8/1976 | Wise | 424/22 |
| 4,069,307 A | 1/1978 | Higuchi et al. | 424/22 |
| 4,093,709 A | 6/1978 | Choi et al. | 424/19 |
| 4,134,742 A | 1/1979 | Schell | |
| 4,186,189 A | 1/1980 | Shalaby | 424/78 |
| 4,249,531 A | 2/1981 | Heller et al. | 128/260 |
| 4,344,431 A | 8/1982 | Yolles | 128/260 |
| 4,346,709 A | 8/1982 | Schmitt | 128/260 |
| 4,351,337 A | 9/1982 | Sidman | 128/260 |
| 4,419,340 A | 12/1983 | Yolles | 424/19 |
| 4,450,150 A | 5/1984 | Sidman | 424/1.1 |

(Continued)

FOREIGN PATENT DOCUMENTS

| | | |
|---|---|---|
| EP | 1374860 | 1/2004 |
| EP | 1601343 | 12/2005 |

(Continued)

OTHER PUBLICATIONS

International Search Report and the Written Opinion of ;the International Searching Authority, or the Declaration documents dated Sep. 1, 2006.

(Continued)

*Primary Examiner* — Paul Dickinson
(74) *Attorney, Agent, or Firm* — Linda S. Li; Jason S. Ngui

(57) ABSTRACT

Described herein are methods for reducing and achieving the desired release of an agent from a delivery system. The desired release kinetics are achieved by exposing the surface of the delivery system with a fluid for a desired period of time.

18 Claims, 5 Drawing Sheets

(56) References Cited

U.S. PATENT DOCUMENTS

| | | | |
|---|---|---|---|
| 4,568,559 A | 2/1986 | Nuwayser et al. | 427/3 |
| 4,612,009 A | 9/1986 | Drobnik et al. | 604/891 |
| 4,623,588 A | 11/1986 | Nuwayser et al. | 428/402.24 |
| 4,650,665 A | 3/1987 | Kronenthal et al. | 424/435 |
| 4,657,543 A | 4/1987 | Langer et al. | 604/891 |
| 4,720,384 A | 1/1988 | Di Luccio et al. | 424/78 |
| 4,767,628 A * | 8/1988 | Hutchinson | 424/426 |
| 4,786,506 A * | 11/1988 | Fontanelli | 424/470 |
| 4,792,448 A | 12/1988 | Ranade | |
| 4,794,001 A | 12/1988 | Mehta et al. | 424/458 |
| 4,795,643 A | 1/1989 | Seth | 424/456 |
| 4,824,937 A | 4/1989 | Deghenghi et al. | 530/326 |
| 4,828,563 A | 5/1989 | Müller-Lierheim | 623/16 |
| 4,832,686 A | 5/1989 | Anderson | 604/49 |
| 4,835,139 A | 5/1989 | Tice et al. | 514/15 |
| 4,839,130 A | 6/1989 | Kaplan et al. | |
| 4,853,225 A | 8/1989 | Wahlig et al. | 424/423 |
| 4,863,735 A | 9/1989 | Kohn et al. | 424/622 |
| 4,883,666 A | 11/1989 | Sabel et al. | 424/422 |
| 4,894,231 A | 1/1990 | Moreau et al. | 424/426 |
| 4,897,268 A | 1/1990 | Tice et al. | |
| 4,898,734 A | 2/1990 | Mathiowitz et al. | |
| 4,902,515 A | 2/1990 | Loomis et al. | |
| 4,952,403 A | 8/1990 | Vallee et al. | 424/422 |
| 4,957,119 A | 9/1990 | De Nijs | 128/832 |
| 4,975,280 A | 12/1990 | Schacht et al. | 424/428 |
| 4,976,949 A | 12/1990 | Meyer et al. | 424/1.1 |
| 4,981,696 A | 1/1991 | Loomis et al. | |
| 5,013,553 A | 5/1991 | Southard et al. | 424/426 |
| 5,019,400 A | 5/1991 | Gombotz et al. | |
| 5,035,891 A | 7/1991 | Runkel et al. | 424/423 |
| 5,110,595 A | 5/1992 | Wang | 424/422 |
| 5,114,719 A | 5/1992 | Sabel et al. | 424/422 |
| 5,134,122 A | 7/1992 | Orsolini | 514/15 |
| 5,141,748 A | 8/1992 | Rizzo | 424/425 |
| 5,150,718 A | 9/1992 | De Nijs | 128/832 |
| 5,152,781 A | 10/1992 | Tang et al. | 606/230 |
| 5,153,002 A | 10/1992 | McMullen | 424/473 |
| 5,164,190 A | 11/1992 | Patel et al. | 424/448 |
| 5,178,874 A | 1/1993 | Kwan et al. | 424/438 |
| 5,187,150 A | 2/1993 | Speiser et al. | 514/2 |
| 5,192,741 A | 3/1993 | Orsolini et al. | 514/4 |
| 5,225,205 A | 7/1993 | Orsolini | 424/489 |
| 5,234,693 A | 8/1993 | Magruder et al. | 424/473 |
| 5,273,752 A | 12/1993 | Ayer et al. | 424/438 |
| 5,310,559 A | 5/1994 | Shah et al. | 424/448 |
| 5,340,586 A | 8/1994 | Pike et al. | 424/426 |
| 5,342,627 A | 8/1994 | Chopra et al. | 424/473 |
| 5,356,635 A | 10/1994 | Raman et al. | 424/484 |
| 5,382,435 A | 1/1995 | Geary et al. | 424/489 |
| 5,395,618 A | 3/1995 | Darougar et al. | 424/427 |
| 5,397,572 A | 3/1995 | Coombes et al. | 424/426 |
| 5,403,595 A | 4/1995 | Kitchell et al. | 424/501 |
| 5,407,609 A | 4/1995 | Tice et al. | 264/46 |
| 5,429,634 A | 7/1995 | Narciso | 604/890.1 |
| 5,429,822 A | 7/1995 | Gresser et al. | 424/426 |
| 5,439,688 A | 8/1995 | Orsolini et al. | 424/489 |
| 5,445,832 A | 8/1995 | Orsolini et al. | 424/491 |
| 5,456,679 A | 10/1995 | Balaban et al. | 604/892.1 |
| 5,456,917 A | 10/1995 | Wise et al. | 424/426 |
| 5,461,140 A | 10/1995 | Heller et al. | 528/425 |
| 5,478,355 A | 12/1995 | Muth et al. | 606/230 |
| 5,486,362 A | 1/1996 | Kitchell et al. | 424/426 |
| 5,518,730 A | 5/1996 | Fuisz | 424/426 |
| 5,531,998 A | 7/1996 | Mares et al. | 424/426 |
| 5,541,172 A | 7/1996 | Labrie et al. | 514/169 |
| 5,543,156 A | 8/1996 | Roorda et al. | 424/484 |
| 5,565,443 A | 10/1996 | Lanquetin et al. | 514/169 |
| 5,571,525 A | 11/1996 | Roorda et al. | 424/426 |
| 5,578,046 A | 11/1996 | Liu et al. | |
| 5,607,417 A | 3/1997 | Batich et al. | 604/890.1 |
| 5,620,697 A | 4/1997 | Tormala et al. | 424/426 |
| 5,626,862 A | 5/1997 | Brem et al. | 424/426 |
| 5,628,993 A | 5/1997 | Yamagata et al. | 424/85.7 |
| 5,630,808 A | 5/1997 | Magruder et al. | 604/892.1 |
| 5,633,000 A | 5/1997 | Grossman et al. | 424/422 |
| 5,633,002 A | 5/1997 | Stricker et al. | 424/426 |
| 5,635,379 A | 6/1997 | Deghenghi | 435/106 |
| 5,637,568 A | 6/1997 | Orsolini et al. | 514/15 |
| 5,646,301 A | 7/1997 | Deghenghi | 548/496 |
| 5,651,986 A | 7/1997 | Brem et al. | 424/484 |
| 5,654,010 A | 8/1997 | Johnson et al. | |
| 5,656,297 A | 8/1997 | Bernstein et al. | |
| 5,668,254 A | 9/1997 | Deghenghi | 530/328 |
| 5,681,568 A | 10/1997 | Goldin et al. | 424/184.1 |
| 5,681,873 A | 10/1997 | Norton et al. | 523/115 |
| 5,700,477 A | 12/1997 | Rosenthal et al. | |
| 5,702,716 A | 12/1997 | Dunn et al. | 424/422 |
| 5,705,191 A | 1/1998 | Price et al. | 424/473 |
| 5,711,960 A | 1/1998 | Shikinami | 424/426 |
| 5,711,968 A | 1/1998 | Tracy et al. | |
| 5,716,644 A | 2/1998 | Zale et al. | |
| 5,747,060 A | 5/1998 | Sackler et al. | 424/426 |
| 5,750,100 A | 5/1998 | Yamagata et al. | 424/85.2 |
| 5,750,143 A | 5/1998 | Rashid et al. | 424/451 |
| 5,756,117 A | 5/1998 | D'Angelo et al. | 424/449 |
| 5,766,242 A | 6/1998 | Wong et al. | 623/4 |
| 5,776,885 A | 7/1998 | Orsolini et al. | 514/2 |
| 5,780,044 A | 7/1998 | Yewey et al. | 424/426 |
| 5,795,957 A | 8/1998 | Deghenghi | 530/329 |
| 5,798,113 A | 8/1998 | Dionne et al. | |
| 5,800,828 A | 9/1998 | Dionne et al. | 424/422 |
| 5,800,829 A | 9/1998 | Dionne et al. | 424/422 |
| 5,807,985 A | 9/1998 | Deghenghi | 530/331 |
| 5,814,342 A | 9/1998 | Okada et al. | 424/493 |
| 5,817,327 A | 10/1998 | Ducheyne et al. | 424/425 |
| 5,817,343 A | 10/1998 | Burke | |
| 5,834,001 A | 11/1998 | Dionne et al. | |
| 5,837,228 A | 11/1998 | Shih et al. | 424/78.37 |
| 5,846,565 A | 12/1998 | Brem et al. | 424/486 |
| 5,851,547 A | 12/1998 | Fujioka et al. | 424/426 |
| 5,869,077 A | 2/1999 | Dionne et al. | |
| 5,871,767 A | 2/1999 | Dionne et al. | |
| 5,872,100 A | 2/1999 | Deghenghi | 514/15 |
| 5,874,098 A | 2/1999 | Stevens et al. | 424/408 |
| 5,874,099 A | 2/1999 | Dionne et al. | |
| 5,876,452 A | 3/1999 | Athanasiou et al. | 623/16 |
| 5,900,425 A | 5/1999 | Kanikanti et al. | 514/356 |
| 5,906,817 A | 5/1999 | Moullier et al. | 424/93.21 |
| 5,912,015 A | 6/1999 | Bernstein et al. | 424/484 |
| 5,916,584 A | 6/1999 | O'Donoghue et al. | 424/426 |
| 5,916,597 A | 6/1999 | Lee et al. | |
| 5,922,253 A | 7/1999 | Herbert et al. | |
| 5,922,340 A | 7/1999 | Berde et al. | 424/426 |
| 5,942,241 A | 8/1999 | Chasin et al. | 424/426 |
| 5,945,115 A | 8/1999 | Dunn et al. | 424/422 |
| 5,945,128 A | 8/1999 | Deghenghi | 424/501 |
| 5,945,284 A | 8/1999 | Livak et al. | |
| 5,958,458 A | 9/1999 | Norling et al. | 424/490 |
| 5,965,125 A | 10/1999 | Mineau-Hanschke | 424/93.21 |
| 5,980,927 A | 11/1999 | Nelson et al. | 424/425 |
| 5,985,305 A | 11/1999 | Peery et al. | 424/422 |
| 6,013,853 A | 1/2000 | Athanasiou et al. | 623/11 |
| 6,045,830 A | 4/2000 | Igari et al. | |
| 6,063,395 A | 5/2000 | Markkula et al. | 424/422 |
| 6,066,325 A | 5/2000 | Wallace et al. | 424/400 |
| 6,077,523 A | 6/2000 | Deghenghi et al. | 424/426 |
| 6,083,523 A | 7/2000 | Dionne et al. | |
| 6,086,908 A | 7/2000 | Gopferich | 424/424 |
| 6,090,925 A | 7/2000 | Woiszwillo et al. | 530/410 |
| 6,096,331 A | 8/2000 | Desai et al. | 424/422 |
| 6,117,441 A | 9/2000 | Moo-Young et al. | 424/422 |
| 6,117,442 A | 9/2000 | Markkula et al. | 424/422 |
| 6,143,314 A | 11/2000 | Chandrashekar et al. | 424/426 |
| 6,153,211 A | 11/2000 | Hubbell et al. | 424/426 |
| 6,156,331 A | 12/2000 | Peery et al. | 424/422 |
| 6,159,490 A | 12/2000 | Deghenghi | 424/426 |
| 6,165,486 A | 12/2000 | Marra et al. | 424/423 |
| 6,183,781 B1 | 2/2001 | Burke | |
| 6,187,329 B1 | 2/2001 | Agrawal et al. | |
| 6,194,000 B1 | 2/2001 | Smith et al. | 424/458 |
| 6,203,813 B1 | 3/2001 | Gooberman | 424/422 |
| 6,214,370 B1 | 4/2001 | Nelson et al. | 424/425 |
| 6,228,111 B1 | 5/2001 | Tormala et al. | 623/1.38 |

| Patent No. | Date | Inventor | Class |
|---|---|---|---|
| 6,245,346 B1 | 6/2001 | Rothen-Weinhold et al. | 424/426 |
| 6,245,347 B1 | 6/2001 | Zhang et al. | 424/449 |
| 6,248,363 B1 | 6/2001 | Patel et al. | 424/497 |
| 6,261,584 B1 | 7/2001 | Peery et al. | 424/422 |
| 6,262,127 B1 | 7/2001 | Acemoglu et al. | 514/772.7 |
| 6,268,053 B1 | 7/2001 | Woiszwillo et al. | 428/402 |
| RE37,410 E | 10/2001 | Brem et al. | 424/484 |
| 6,296,842 B1 | 10/2001 | Jaworowicz et al. | |
| 6,303,137 B1 | 10/2001 | Dittgen et al. | |
| 6,306,423 B1 | 10/2001 | Donovan et al. | 424/423 |
| 6,309,660 B1 | 10/2001 | Hsu et al. | |
| 6,312,708 B1 | 11/2001 | Donovan et al. | 424/423 |
| 6,319,512 B1 | 11/2001 | Rothen-Weinhold et al. | 424/425 |
| 6,331,313 B1 | 12/2001 | Wong et al. | 424/427 |
| 6,365,172 B1 | 4/2002 | Barrows | 424/423 |
| 6,368,630 B1 | 4/2002 | Bernstein et al. | 424/486 |
| 6,375,972 B1 | 4/2002 | Guo et al. | 424/423 |
| 6,379,962 B1 | 4/2002 | Holy et al. | |
| 6,383,509 B1 | 5/2002 | Donovan et al. | 424/423 |
| 6,395,292 B2 | 5/2002 | Peery et al. | 424/422 |
| 6,406,719 B1 | 6/2002 | Farrar et al. | 424/489 |
| 6,410,056 B1 | 6/2002 | Setterstrom et al. | 424/501 |
| 6,419,655 B1 | 7/2002 | Nett et al. | 604/57 |
| 6,419,920 B1 | 7/2002 | Mineau-Hanschke | 424/93.21 |
| 6,419,954 B1 | 7/2002 | Chu et al. | 424/465 |
| 6,447,542 B1 | 9/2002 | Weadock | 623/11.11 |
| 6,447,796 B1 | 9/2002 | Vook et al. | 424/422 |
| 6,455,526 B1 | 9/2002 | Kohn et al. | 514/248 |
| 6,472,210 B1 | 10/2002 | Holy et al. | |
| 6,475,779 B2 | 11/2002 | Mathiowitz et al. | 435/320.1 |
| 6,479,065 B2 | 11/2002 | Jaworowicz et al. | |
| 6,506,399 B2 | 1/2003 | Donovan | 424/423 |
| 6,506,410 B1 | 1/2003 | Park et al. | 424/489 |
| 6,514,516 B1 | 2/2003 | Chasin et al. | 424/426 |
| 6,514,533 B1 | 2/2003 | Burke et al. | 424/486 |
| 6,521,259 B1 | 2/2003 | Chasin et al. | 424/489 |
| 6,524,607 B1 | 2/2003 | Goldenheim et al. | 424/426 |
| 6,528,080 B2 | 3/2003 | Dunn et al. | 424/426 |
| 6,528,097 B1 | 3/2003 | Vaughn et al. | 424/501 |
| 6,545,097 B2 | 4/2003 | Pinchuk et al. | 525/240 |
| 6,555,525 B2 | 4/2003 | Burke | 514/44 |
| 6,565,777 B2 | 5/2003 | Farrar et al. | 264/4.1 |
| 6,569,463 B2 | 5/2003 | Patel et al. | 424/497 |
| 6,576,258 B1 | 6/2003 | Kofler et al. | 424/458 |
| 6,576,263 B2 | 6/2003 | Truong et al. | 424/489 |
| 6,579,533 B1 | 6/2003 | Tormala et al. | 424/426 |
| 6,585,993 B2 | 7/2003 | Donovan | |
| 6,596,308 B2 | 7/2003 | Gutierrez-Rocca et al. | 424/451 |
| 6,599,529 B1 | 7/2003 | Skinhøj et al. | 424/458 |
| 6,620,422 B1 | 9/2003 | Maquin et al. | 424/422 |
| 6,623,749 B2 | 9/2003 | Williams et al. | 424/423 |
| 6,627,600 B2 | 9/2003 | Boutignon | 514/2 |
| 6,632,446 B1 | 10/2003 | Hubbell et al. | 424/423 |
| 6,641,831 B1 | 11/2003 | Schierholz | 424/422 |
| 6,648,849 B2 | 11/2003 | Tenhuisen et al. | 604/60 |
| 6,669,955 B2 | 12/2003 | Chungi et al. | 424/464 |
| 6,669,959 B1 | 12/2003 | Adjei et al. | 424/489 |
| 6,680,065 B2 | 1/2004 | Podszun | 424/408 |
| 6,696,073 B2 | 2/2004 | Boyce et al. | 424/422 |
| 6,702,803 B2 | 3/2004 | Kupperblatt et al. | 604/890.1 |
| 6,719,935 B2 | 4/2004 | Tunc | |
| 6,719,989 B1 | 4/2004 | Matsushima et al. | 424/422 |
| 6,746,661 B2 | 6/2004 | Kaplan | 424/1.29 |
| 6,749,866 B2 | 6/2004 | Bernstein et al. | 424/484 |
| 6,756,049 B2 | 6/2004 | Brubaker et al. | 424/428 |
| 6,756,058 B2 | 6/2004 | Brubaker et al. | 424/473 |
| 6,767,550 B1 | 7/2004 | Genin et al. | |
| 6,774,155 B2 | 8/2004 | Martakos et al. | 522/157 |
| 6,793,938 B2 | 9/2004 | Sankaram | 424/489 |
| 6,828,357 B1 | 12/2004 | Martin et al. | 523/124 |
| 6,835,194 B2 | 12/2004 | Johnson et al. | 604/890.1 |
| 6,844,010 B1 | 1/2005 | Setterstrom et al. | 424/501 |
| 6,855,331 B2 | 2/2005 | Vook et al. | 424/422 |
| 6,855,770 B2 | 2/2005 | Pinchuk et al. | 525/240 |
| 6,858,222 B2 | 2/2005 | Nelson et al. | |
| 6,869,588 B2 | 3/2005 | Weller et al. | 424/1.29 |
| 6,887,270 B2 | 5/2005 | Miller et al. | 623/23.7 |
| 6,902,743 B1 | 6/2005 | Setterstrom et al. | 424/489 |
| 6,913,760 B2 | 7/2005 | Carr et al. | 424/484 |
| 6,913,762 B2 | 7/2005 | Caplice et al. | 424/423 |
| 6,913,764 B2 | 7/2005 | Vogt et al. | |
| 6,913,767 B1 | 7/2005 | Cleland et al. | 424/468 |
| 6,916,483 B2 | 7/2005 | Ralph et al. | 424/422 |
| 6,921,541 B2 | 7/2005 | Chasin et al. | 424/426 |
| 6,923,988 B2 | 8/2005 | Patel et al. | 424/497 |
| 6,926,903 B2 | 8/2005 | Pirhonen et al. | 424/426 |
| 6,939,375 B2 | 9/2005 | Sirhan et al. | 623/1.42 |
| 6,945,949 B2 | 9/2005 | Wilk | |
| 6,960,351 B2 | 11/2005 | Dionne et al. | 424/422 |
| 6,991,802 B1 | 1/2006 | Ahola et al. | |
| 7,034,050 B2 | 4/2006 | Deghenghi | 514/419 |
| 7,048,946 B1 | 5/2006 | Wong et al. | 424/486 |
| 7,049,348 B2 | 5/2006 | Evans et al. | 521/82 |
| 7,074,426 B2 | 7/2006 | Kochinke | 424/423 |
| 7,097,850 B2 | 8/2006 | Chappa et al. | |
| 7,101,394 B2 | 9/2006 | Hamm et al. | |
| 7,101,567 B1 | 9/2006 | Sano et al. | 424/472 |
| 7,153,519 B2 | 12/2006 | Hubbell et al. | 435/6 |
| 7,163,691 B2 | 1/2007 | Knaack et al. | 424/422 |
| 7,169,405 B2 | 1/2007 | Trieu | 424/426 |
| 7,192,604 B2 | 3/2007 | Brown et al. | 424/422 |
| 7,226,612 B2 | 6/2007 | Sohier et al. | |
| 7,279,175 B2 | 10/2007 | Chen et al. | |
| 7,303,758 B2 | 12/2007 | Falotico et al. | |
| 2001/0009769 A1 | 7/2001 | Williams et al. | 435/135 |
| 2001/0026804 A1 | 10/2001 | Boutignon | 424/422 |
| 2002/0028244 A1 | 3/2002 | Donovan et al. | 424/486 |
| 2002/0037309 A1 | 3/2002 | Jaworowicz et al. | |
| 2002/0054900 A1 | 5/2002 | Kamath et al. | |
| 2002/0064547 A1 | 5/2002 | Chern et al. | 424/426 |
| 2002/0090398 A1 | 7/2002 | Dunn et al. | 424/486 |
| 2002/0098237 A1 | 7/2002 | Donovan et al. | 424/484 |
| 2002/0107330 A1 | 8/2002 | Pinchuk et al. | 525/242 |
| 2002/0119179 A1 | 8/2002 | Rezania et al. | 424/426 |
| 2002/0131953 A1 | 9/2002 | Takashima et al. | 424/85.1 |
| 2002/0131988 A1 | 9/2002 | Foster et al. | 424/422 |
| 2002/0150603 A1 | 10/2002 | Dionne et al. | |
| 2002/0160033 A1 | 10/2002 | Caplice et al. | 424/423 |
| 2002/0168393 A1 | 11/2002 | Sugimoto | 424/423 |
| 2003/0004491 A1 | 1/2003 | Tenhuisen et al. | 604/502 |
| 2003/0007992 A1 | 1/2003 | Gibson | |
| 2003/0031700 A1 | 2/2003 | Hammang et al. | |
| 2003/0039676 A1 | 2/2003 | Boyce et al. | 424/423 |
| 2003/0049320 A1 | 3/2003 | Bhagwatwar et al. | 424/486 |
| 2003/0060871 A1 | 3/2003 | Hill et al. | |
| 2003/0093157 A1 | 5/2003 | Casares et al. | 623/23.73 |
| 2003/0095995 A1 | 5/2003 | Wong et al. | 424/426 |
| 2003/0104029 A1 | 6/2003 | Pirhonen et al. | 424/426 |
| 2003/0108588 A1 | 6/2003 | Chen et al. | |
| 2003/0133964 A1 | 7/2003 | Dunn et al. | 424/428 |
| 2003/0143258 A1 | 7/2003 | Knaack et al. | 424/426 |
| 2003/0152634 A1 | 8/2003 | Bodmeier | 424/489 |
| 2003/0153983 A1 | 8/2003 | Miller et al. | 623/23.7 |
| 2003/0158598 A1 | 8/2003 | Ashton et al. | |
| 2003/0161881 A1 | 8/2003 | Hansen et al. | 424/468 |
| 2003/0165555 A1 | 9/2003 | Ding et al. | 424/422 |
| 2003/0170288 A1 | 9/2003 | Carr et al. | 424/426 |
| 2003/0185872 A1 | 10/2003 | Kochine | 424/426 |
| 2003/0224033 A1 | 12/2003 | Li et al. | 424/423 |
| 2003/0229390 A1 | 12/2003 | Ashton et al. | |
| 2003/0232122 A1 | 12/2003 | Chappa et al. | |
| 2003/0235602 A1 | 12/2003 | Schwarz | |
| 2004/0006146 A1 | 1/2004 | Evans et al. | 521/50 |
| 2004/0009228 A1 | 1/2004 | Tormala et al. | 424/486 |
| 2004/0010048 A1 | 1/2004 | Evans et al. | 521/50 |
| 2004/0013703 A1 | 1/2004 | Ralph et al. | 424/426 |
| 2004/0033250 A1 | 2/2004 | Patel | 424/423 |
| 2004/0034337 A1 | 2/2004 | Boulais et al. | |
| 2004/0086569 A1 | 5/2004 | Sparer et al. | 424/486 |
| 2004/0115236 A1 | 6/2004 | Chan et al. | 424/423 |
| 2004/0115241 A1 | 6/2004 | Calhoun et al. | 424/426 |
| 2004/0126404 A1 | 7/2004 | Campbell et al. | 424/422 |
| 2004/0137065 A1 | 7/2004 | Vogt et al. | |
| 2004/0142011 A1 | 7/2004 | Nilsson et al. | 424/422 |
| 2004/0143221 A1 | 7/2004 | Shadduck | 604/175 |
| 2004/0151753 A1 | 8/2004 | Chen et al. | 424/426 |

| | | | | | | |
|---|---|---|---|---|---|---|
| 2004/0166141 A1 | 8/2004 | Cerami et al. ............... 424/426 | | 2006/0093643 A1 | 5/2006 | Stenzel |
| 2004/0175406 A1 | 9/2004 | Schwart ....................... 424/423 | | 2006/0105018 A1 | 5/2006 | Epstein et al. |
| 2004/0175410 A1 | 9/2004 | Ashton et al. | | 2006/0115515 A1 | 6/2006 | Pirhonen et al. ............ 424/426 |
| 2004/0199241 A1* | 10/2004 | Gravett et al. .............. 623/1.13 | | 2006/0134168 A1 | 6/2006 | Chappa et al. |
| 2004/0202691 A1 | 10/2004 | Richard ........................ 424/423 | | 2006/0140999 A1 | 6/2006 | Lendlein et al. ............. 424/422 |
| 2004/0208910 A1 | 10/2004 | Ashton et al. | | 2006/0147491 A1 | 7/2006 | DeWitt et al. ................ 424/426 |
| 2004/0208985 A1 | 10/2004 | Rowan et al. | | 2006/0159721 A1 | 7/2006 | Siegel et al. ................. 424/426 |
| 2004/0219180 A1 | 11/2004 | Gambale et al. .............. 424/423 | | 2006/0165754 A1 | 7/2006 | Ranade ........................ 424/423 |
| 2004/0224000 A1 | 11/2004 | Deghenghi .................... 424/423 | | 2006/0171980 A1 | 8/2006 | Helmus et al. ............... 424/422 |
| 2004/0234572 A1 | 11/2004 | Martinod et al. | | 2006/0171981 A1 | 8/2006 | Richard et al. ............... 424/422 |
| 2004/0234576 A1 | 11/2004 | Martin et al. ................. 424/426 | | 2006/0171987 A1 | 8/2006 | Mauriac et al. ............... 424/426 |
| 2004/0241204 A1 | 12/2004 | Martinod et al. .............. 424/426 | | 2006/0177480 A1 | 8/2006 | Sung et al. |
| 2004/0243097 A1 | 12/2004 | Falotico et al. | | 2006/0193888 A1 | 8/2006 | Lye et al. |
| 2004/0247643 A1 | 12/2004 | Martinod et al. .............. 424/426 | | 2006/0195176 A1 | 8/2006 | Bates et al. |
| 2004/0259768 A1 | 12/2004 | Lauermann ..................... 514/2 | | 2006/0198868 A1 | 9/2006 | DeWitt et al. ................ 424/426 |
| 2004/0260268 A1 | 12/2004 | Falotico et al. | | 2006/0204533 A1 | 9/2006 | Hsu et al. |
| 2004/0265383 A1 | 12/2004 | Cui et al. ..................... 424/469 | | 2006/0204548 A1 | 9/2006 | Nivaggioli et al. ........... 424/427 |
| 2004/0265475 A1 | 12/2004 | Hossainy et al. .............. 427/2.1 | | 2006/0210594 A1 | 9/2006 | Trieu ............................ 424/422 |
| 2005/0002895 A1 | 1/2005 | Corcoran ................... 424/78.17 | | 2006/0210598 A1 | 9/2006 | Evans et al. ................. 424/422 |
| 2005/0002986 A1 | 1/2005 | Falotico et al. | | 2006/0210604 A1 | 9/2006 | Dadey et al. |
| 2005/0013840 A1 | 1/2005 | Potter et al. ................. 424/422 | | 2006/0216323 A1 | 9/2006 | Knaack et al. ............... 424/422 |
| 2005/0019367 A1 | 1/2005 | Booth et al. ................. 424/426 | | 2006/0222681 A1 | 10/2006 | Richard ........................ 424/426 |
| 2005/0025801 A1 | 2/2005 | Richard et al. ............... 424/423 | | 2006/0240071 A1 | 10/2006 | Lerner et al. |
| 2005/0025802 A1 | 2/2005 | Richard et al. ............... 424/423 | | 2006/0246110 A1 | 11/2006 | Brandon et al. |
| 2005/0025803 A1 | 2/2005 | Richard et al. ............... 424/423 | | 2006/0246112 A1 | 11/2006 | Snyder et al. |
| 2005/0025806 A1 | 2/2005 | Brandon et al. ............... 424/423 | | 2006/0257448 A1 | 11/2006 | Weber ........................ 424/426 |
| 2005/0027283 A1 | 2/2005 | Richard et al. ............... 604/890.1 | | 2006/0257451 A1 | 11/2006 | Varner et al. |
| 2005/0031667 A1 | 2/2005 | Patel et al. .................... 424/426 | | 2007/0009564 A1 | 1/2007 | McClain et al. .............. 424/423 |
| 2005/0031668 A1 | 2/2005 | Patel et al. .................... 424/426 | | 2007/0016163 A1 | 1/2007 | Santini et al. ................. 604/500 |
| 2005/0031669 A1 | 2/2005 | Shafie et al. ................. 424/426 | | 2007/0020307 A1 | 1/2007 | Zhong et al. ................. 424/423 |
| 2005/0037047 A1 | 2/2005 | Song ............................ 424/423 | | 2007/0048350 A1 | 3/2007 | Falotico et al. |
| 2005/0042253 A1 | 2/2005 | Farrar et al. ................. 424/426 | | 2007/0053952 A1 | 3/2007 | Chen et al. ................... 424/423 |
| 2005/0060019 A1 | 3/2005 | Gambale et al. .............. 623/1.11 | | 2007/0059336 A1 | 3/2007 | Hughes et al. |
| 2005/0065214 A1 | 3/2005 | Kronenthal ................... 514/557 | | 2007/0059369 A1 | 3/2007 | Mauvernay |
| 2005/0070989 A1 | 3/2005 | Lye et al. | | 2007/0077272 A1 | 4/2007 | Li et al. |
| 2005/0079199 A1 | 4/2005 | Heruth et al. ................. 424/423 | | 2007/0098753 A1 | 5/2007 | Falotico et al. |
| 2005/0079200 A1 | 4/2005 | Rathenow et al. ........... 424/423 | | 2007/0116736 A1 | 5/2007 | Argentieri et al. |
| 2005/0079216 A1 | 4/2005 | Petereit et al. | | 2007/0116737 A1 | 5/2007 | Favis et al. |
| 2005/0100582 A1 | 5/2005 | Stenzel | | 2007/0116738 A1 | 5/2007 | Mauriac |
| 2005/0118229 A1 | 6/2005 | Boiarski | | 2007/0154524 A1 | 7/2007 | Kauper et al. |
| 2005/0129728 A1 | 6/2005 | Martinod et al. | | 2007/0196423 A1 | 8/2007 | Ruane et al. |
| 2005/0147673 A1 | 7/2005 | Staniforth et al. ............ 424/464 | | 2007/0202147 A1 | 8/2007 | Kleiner et al. |
| 2005/0158360 A1 | 7/2005 | Falotico et al. | | 2007/0212388 A1 | 9/2007 | Patravale et al. |
| 2005/0181015 A1 | 8/2005 | Zhong ......................... 424/426 | | 2007/0224239 A1 | 9/2007 | Behan et al. |
| 2005/0181048 A1 | 8/2005 | Romero ........................ 424/469 | | 2007/0243230 A1 | 10/2007 | De Juan, Jr. et al. |
| 2005/0182485 A1 | 8/2005 | Falotico et al. | | 2007/0248637 A1 | 10/2007 | Chappa et al. |
| 2005/0186239 A1 | 8/2005 | Hunter et al. ................ 424/423 | | 2007/0254103 A1 | 11/2007 | Sohier et al. |
| 2005/0186251 A1 | 8/2005 | Pirhonen et al. ............. 424/426 | | 2007/0298073 A1 | 12/2007 | Whitcup et al. |
| 2005/0191333 A1 | 9/2005 | Hsu | | 2007/0298074 A1 | 12/2007 | Robinson et al. |
| 2005/0191334 A1 | 9/2005 | Wong et al. ................. 424/426 | | 2008/0003256 A1 | 1/2008 | Martens et al. |
| 2005/0202059 A1 | 9/2005 | Falotico et al. | | 2008/0014241 A1 | 1/2008 | DesNoyer et al. |
| 2005/0208092 A1 | 9/2005 | Falotico et al. | | 2008/0020012 A1 | 1/2008 | Ju et al. |
| 2005/0208095 A1 | 9/2005 | Hunter et al. ................ 424/423 | | 2008/0026031 A1 | 1/2008 | Patel et al. |
| 2005/0208098 A1 | 9/2005 | Castro et al. | | 2008/0026034 A1 | 1/2008 | Cook et al. |
| 2005/0244447 A1 | 11/2005 | Heath ........................... 424/422 | | 2008/0031922 A1 | 2/2008 | Riihimaki |
| 2005/0244461 A1 | 11/2005 | Nivaggioli et al. ........... 424/427 | | 2008/0038354 A1 | 2/2008 | Slager et al. |
| 2005/0244465 A1 | 11/2005 | Nivaggioli et al. | | 2008/0051866 A1 | 2/2008 | Chen et al. |
| 2005/0244467 A1 | 11/2005 | Nivaggioli et al. | | 2008/0057101 A1 | 3/2008 | Roorda |
| 2005/0244468 A1 | 11/2005 | Huang et al. ................ 424/427 | | 2008/0057102 A1 | 3/2008 | Roorda |
| 2005/0244469 A1 | 11/2005 | Whitcup et al. ............. 424/427 | | 2008/0057103 A1 | 3/2008 | Roorda |
| 2005/0244506 A1 | 11/2005 | Burke et al. ................. 424/489 | | 2008/0058733 A1 | 3/2008 | Vogt et al. |
| 2005/0244775 A1 | 11/2005 | Falotico et al. .............. 424/423 | | 2008/0075753 A1 | 3/2008 | Chappa |
| 2005/0249776 A1 | 11/2005 | Chen et al. .................. 424/423 | | 2008/0091222 A1 | 4/2008 | Deusch et al. |
| 2005/0271698 A1 | 12/2005 | Bucay-Couto et al. ........ 424/423 | | 2008/0166391 A1 | 7/2008 | Gibson et al. |
| 2005/0271706 A1 | 12/2005 | Anderson et al. | | 2008/0254086 A1 | 10/2008 | Brown et al. |
| 2006/0002977 A1 | 1/2006 | Dugan .......................... 424/426 | | 2009/0074786 A1* | 3/2009 | Dor et al. ..................... 424/141.1 |
| 2006/0002979 A1 | 1/2006 | Ashammakhi et al. ....... 424/426 | | | | |
| 2006/0003008 A1 | 1/2006 | Gibson et al. ................. 424/486 | | | FOREIGN PATENT DOCUMENTS | |
| 2006/0008503 A1 | 1/2006 | Shanley et al. | | FR | 2762318 | 10/1998 |
| 2006/0013835 A1 | 1/2006 | Anderson et al. | | GB | 2103927 | 3/1983 |
| 2006/0013849 A1 | 1/2006 | Strickler et al. .............. 424/422 | | GB | 2249724 | 5/1992 |
| 2006/0013854 A1 | 1/2006 | Strickler et al. .............. 424/423 | | WO | WO 93/17662 | 9/1993 |
| 2006/0018948 A1 | 1/2006 | Guire et al. .................. 424/426 | | WO | WO 98/09613 | 3/1998 |
| 2006/0029637 A1 | 2/2006 | Tice et al. .................... 424/423 | | WO | WO-03/000156 A1 | 1/2003 |
| 2006/0029678 A1 | 2/2006 | Deghenghi et al. .......... 424/489 | | WO | WO/03/094888 | 11/2003 |
| 2006/0039946 A1 | 2/2006 | Heruth et al. ................ 424/422 | | WO | WO 2004/078160 | 9/2004 |
| 2006/0051390 A1 | 3/2006 | Schwarz ....................... 424/426 | | WO | WO 2005/016396 | 2/2005 |
| 2006/0073182 A1 | 4/2006 | Wong et al. ................. 424/426 | | WO | WO 2006012667 | 2/2006 |
| 2006/0083767 A1 | 4/2006 | Deusch ......................... 424/422 | | WO | WO-2006/078320 A2 | 7/2006 |

| WO | WO-2011/035013 A2 | 3/2011 |
| WO | WO-2011/037953 A2 | 3/2011 |
| WO | WO-2011/037955 A1 | 3/2011 |

OTHER PUBLICATIONS

Yamakawa et al., "Sustained Release of Insulin by Double-Layered Implant Using Poly(D,L-Lactic Acid)," *J Pharm Sci.* 79(6): 505-509, 1990.

Bhardwaj, et al., "In vitro evaluation of Poly(d,l-lactide-co-glycolide) polymer-based implants containing the alpha-melanocyte stimulating hormone analog, Melanotan-I," *Journal of Controlled Release*, 45:49-55 (1997).

Steendam, "SynBiosys™ Biodegradable Polymeric Drug Delivery System," *Business Briefing: Pharma Outsourcing*, p. 1-5 (2005).

Varner et al., "Coatings: Sustained-Release Drug Delivery for Retinal Disease," *Medical Device & Diagnostic Industry Magazine*, published Jul. 2005.

Mallapragada et al., "Crystal Dissolution-Controlled Release Systems. II. Metronidazole Release From Semicrystalline Poly(vinyl alcohol) systems," *J Biomed Mater Res.*,36(1):125-30 (1997).

Notice of Abandonment issued on Aug. 8, 2012 for U.S. Appl. No. 12/887,877, filed Aug. 3, 2005 (Inventor—Biggs et al.; pp. 1-2).

Non Final Office Action issued on Jun. 27, 2012 for U.S. Appl. No. 12/887,893, filed Sep. 22, 2010 (Inventor—Biggs et al.; pp. 1-8).

Response to Office Action filed on Sep. 26, 2012 for U.S. Appl. No. 12/887,893, filed Sep. 22, 2010 (Inventor—Biggs et al.; pp. 1-8).

Supplemental Response to Office Action filed on Oct. 10, 2012 for U.S. Appl. No. 12/887,893, filed Sep. 22, 2010 (Inventor—Biggs et al.; pp. 1-5).

International Preliminary Report on Patentability issued on Apr. 5, 2012 for Intl. App. No. PCT/US2010/049753, filed on Sep. 22, 2010 (Inventor—D. Biggs; Applicant—Evonik Degussa Corp., Inc.; pp. 1-8).

International Preliminary Report on Patentability issued on Apr. 5, 2012 for Intl. App. No. PCT/US2010/049750, filed on Sep. 22, 2010 (Inventor—D. Biggs; Applicant—Evonik Degussa Corp., Inc.; pp. 1-10).

Official Action issued by Canadian Intellectual Property Office on Aug. 1, 2012 for CA Pat. App. No. 2,575,988 which is national phase of PCT/US2005/27477 filed Aug. 3, 2005 (Inventor—Staas et al.; Applicant—Brookwood Pharmacueticals Inc.; pp. 1-2).

Intention to grant European patent issued by European Patent Office on Nov. 15, 2012 for EP Pat. App. No. 05856905.4, which is national phase of PCT/US2005/27477 filed Aug. 3, 2005 (Inventor—Staas et al.; Applicant—Brookwood Pharmacueticals Inc.; pp. 1-6).

Preliminary Amendment filed on Nov. 19, 2012 for EP Pat. App. No. 10760198.1, regional phase of Intl. App. No. PCT/US2010/049750, filed on Sep. 22, 2010 (Inventor—D. Biggs; Applicant—Evonik Degussa Corp.; pp. 1-6).

Int'l Search Report & Written Opinion in PCT/US2010/049753, issued Dec. 23, 2010.

Response to Official Report filed by Applicant on Aug. 19, 2010 for AU Pat. App. No. 2005325213, which is national phase of PCT/US2005/27477 filed Aug. 3, 2005 (Inventor—Staas et al.; Applicant—SurModics Pharmacueticals Inc.; pp. 1-5).

Examiner's Report issued by Australian Patent Office on Aug. 19, 2009 for AU Pat. App. No. 2005325213, which is national phase of PCT/US2005/27477 filed Aug. 3, 2005 (Inventor—Staas et al.; Applicant—SurModics Pharmacueticals Inc.; pp. 1-3).

Response to Official Action filed by Applicant on May 25, 2011 for CA Pat. App. No. 2,575,988 which is national phase of PCT/US2005/27477 filed Aug. 3, 2005 (Inventor—Staas et al.; Applicant—Brookwood Pharmacueticals Inc.; pp. 1-8).

Response to Official Action filed by Applicant on Jul. 28, 2010 for CA Pat. App. No. 2,575,988 which is national phase of PCT/US2005/27477 filed Aug. 3, 2005 (Inventor—Staas et al.; Applicant—Brookwood Pharmacueticals Inc.; pp. 1-13).

Communication issued by European Patent Office on Nov. 26, 2010 for EP Pat. App. No. 05856905.4, which is national phase of PCT/US2005/27477 filed Aug. 3, 2005 (Inventor—Staas et al.; Applicant—Brookwood Pharmacueticals Inc.; pp. 1-3).

Reply to Communication filed by Applicant on Apr. 6, 2011 for EP Pat. App. No. 05856905.4, which is national phase of PCT/US2005/27477 filed Aug. 3, 2005 (Inventor—Staas et al.; Applicant—Brookwood Pharmacueticals Inc.; pp. 1-10).

Communication issued by European Patent Office on Apr. 21, 2011 for EP Pat. App. No. 05856905.4, which is national phase of PCT/US2005/27477 filed Aug. 3, 2005 (Inventor—Staas et al.; Applicant—Brookwood Pharmacueticals Inc.; pp. 1-3).

Requirement for Restriction/Election issued by United States Patent and Trademark Office on Oct. 7, 2011 for U.S. Appl. No. 12/887,877, filed Sep. 22, 2010 (Inventor—Biggs; pp. 1-10).

International Preliminary Report on Patentability issued by International Bureau of WIPO on Feb. 6, 2007 for Intl. App. No. PCT/US2005/027477, filed on Sep. 3, 2005 (Inventor—Staas et al.; Applicant—Brookwood Pharmacueticals, Inc.; pp. 1-6).

Blanco-Prieto, M. et al., "Importance of single or blended polymer types for controlled in vitro release and plasma levels of a somatostatin analogue entrapped in PLA/PLGA microspheres," J Control Release, 2004, 96: 437-448.

Kim, H. et al., "Comparative study on sustained release of human growth hormone from semi-crystalline poly(l-lactic acid) and amorphous poly(d,l-lactic-co-glycolic acid) microspheres: morphological effect on protein release," J Control Release, 2004, 98: 115-125.

Li, Y. and Zhu, J., "Modulation of combined-release behaviors from a novel "tablets-in-capsule system"," J Control Release, 2004, 95: 381-389.

Siepmann, N. et al., "Effect of the size of biodegradable microparticles on drug release: experiment and theory," J Control Release, 2004, 96: 123-134.

Response to Restriction/Election filed on Oct. 31, 2011 for U.S. Appl. No. 12/887,877, filed Sep. 22, 2010 (Inventor—Biggs; pp. 1-4).

Official Action issued by Canadian Intellectual Property Office on Sep. 27, 2011 for CA Pat. App. No. 2,575,988 which is national phase of PCT/US2005/27477 filed Aug. 3, 2005 (Inventor—Staas et al.; Applicant—Brookwood Pharmacueticals Inc.; pp. 1-2).

Office Action issued in Canadian Patent Application No. 2,575,988; dated Dec. 9, 2010.

Notice of Acceptance issued in Australian Application No. 2005325213, dated Sep. 21, 2010.

Examiner's Report issued in Canadian Patent Application No. 2,575,988; dated Feb. 2, 2010.

Response to Official Action filed Mar. 26, 2012 for CA Pat. App. No. 2,575,988 which is national phase of PCT/US2005/27477 filed Aug. 3, 2005 (Inventor—Staas et al.; Applicant—Brookwood Pharmaceuticals Inc.; pp. 1-8).

Reply to Communication filed on Feb. 20, 2012 for EP Pat. App. No. 05856905.4, which is national phase of PCT/US2005/27477 filed Aug. 3, 2005 (Inventor—Staas et al.; Applicant—Brookwood Pharmaceuticals Inc.; pp. 1-10).

Response to Restriction/Election filed on Jun. 13, 2013 for U.S. Appl. No. 12/887,893, filed Sep. 22, 2010 (Inventor—Biggs et al.; pp. 1-3).

Non-Final Office Action issued on Jan. 19, 2012 for U.S. Appl. No. 12/887,877, filed Sep. 22, 2010 (Inventor—Biggs et al., pp. 1-10).

International Search Report and Written Opinion issued by International Searching Authority of WIPO on Dec. 6, 2011 for Intl. App. No. PCT/US2011/049750, filed on Sep. 22, 2010 (Inventor—D. Biggs; Applicant—Surmodics Pharmaceuticals, Inc.; pp. 1-14).

Requirement for Restriction/Election issued by United States Patent and Trademark Office on Feb. 13, 2012 for U.S. Appl. No. 12/887,893, filed Sep. 22, 2010 (Inventor—Biggs et al.; pp. 1-7).

* cited by examiner

METHODS FOR MANUFACTURING DELIVERY DEVICES AND DEVICES THEREOF

CROSS REFERENCE TO RELATED APPLICATIONS

This application claims the benefit of U.S. Provisional Application Ser. No. 60/599,174, filed on Aug. 4, 2004, which application is hereby incorporated by reference in its entirety for all of its teachings.

BACKGROUND

In the realm of pharmaceutical formulations, there is a class of drug-delivery formulations that are designed to release bioactive agents for a desired period of time following a single administration. Depot formulation is one name used to describe these long-acting formulations. Depot formulations can be fabricated in many ways. A typical formulation approach to prepare a depot formulation or implant is by manufacturing a solid matrix that includes a bioactive agent and a polymeric excipient. The purpose of the polymeric excipient of the implant is to restrict the influx of water, which in turns controls the dissolution of the bioactive agent followed by the release of the bioactive agent from the implant matrix. In addition to the physical and chemical properties of the bioactive agent, the amount of bioactive agent in the implant contributes to the rate of bioactive agent release. That is, increasing the amount of bioactive agent increases the rate of release. Unfortunately, some implant formulations require a high amount of bioactive agent inside in order to have enough bioactive agent available to achieve dose and duration requirements for a particular medical indication. A high amount of bioactive agent incorporated inside the implant, however, may cause the release the bioactive agent to occur too fast or even at an uncontrollable rate.

It is an object of the present invention to provide delivery systems with a controlled release even at high loadings. Moreover, it is an object of the present invention to provide delivery systems and methods for their manufacture having decreased microbial contamination. It is a further object of the present invention to provide delivery systems having a smooth or smoother (than untreated) surface for easy administration. It is another object of the present invention to provide delivery systems where the delivery rate can be adjusted by modifying the surface.

The present invention solves this rapid release problem, i.e., the bioactive agent being released too fast, by modifying the polymeric surface or polymer skin of a delivery system by exposing the polymer present in the system to a fluid. The fluid-treatment causes the properties of the polymer on the surface of the delivery system to change such that the system is less permeable. It is the fluid treatment of the delivery system that is responsible for the slower release of the bioactive agent from the delivery system. In addition, the delivery systems produced herein are generally smoother than other delivery systems, which can facilitate the administration of the system to the subject. Additionally, the methods described herein can lower the bioburden of the delivery system by reducing the presence of microorganisms present on the system. Finally, the delivery systems produced herein have increased tensile strength, i.e., reduced friability, which aids in the preparation and administration of the system.

SUMMARY

Described herein are methods for reducing and achieving the desired release of an agent from a delivery system. The desired release kinetics are achieved by exposing the surface of the delivery system to a fluid for a predetermined period of time. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
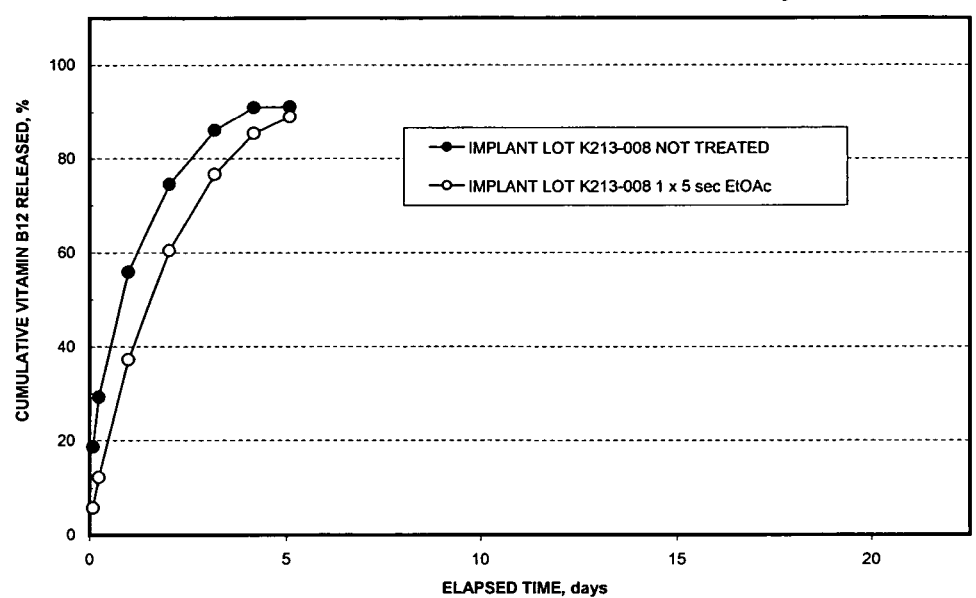
FIG. 1 shows the in vitro release of vitamin $B_{12}$ (45 wt %) from poly(DL-lactide) implants with and without fluid exposure.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

A weight percent of a component, unless specifically stated to the contrary, is based on the total weight of the formulation or composition in which the component is included.

By "contacting" is meant an instance of exposure by close physical contact of at least one substance to another substance.

By "combination" when referring to components of the polymer, it is meant a physical mixture (blend), a non-homogeneous mixture, multiple layers of the individual polymers, or a copolymer thereof.

The term "admixing" is defined as mixing the two components together. Depending upon the components to be admixed, there may or may not be a chemical or physical interaction between two or more components.

By "sufficient amount" and "sufficient time" means an amount and time needed to achieve the desired result or results.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are methods for producing delivery systems. As used herein, "delivery systems" refer to both devices and coated articles as defined herein. The methods described herein allow for the manufacture of controlled-release, extended-release, modified-release, sustained-release, pulsatile-release, delayed-release, or programmed-release delivery of an agent. The term "delivery" as used herein includes all different types of delivery. In a further aspect, the delivery system is a device. In another further aspect, the delivery system is a coated article.

The term "device" is any formulation or article that is greater than 1 mm in length in at least one dimension of the device. The device can comprise a polymer and an agent. In a further aspect, the device has one dimension that is from 1 mm to 50 mm, 1.2 mm to 45 mm, 1.4 mm to 42 mm, 1.6 mm to 40 mm, 1.8 mm to 38 mm, or 2.0 mm to 36 mm, 5.0 mm to 33 mm, or 10 mm to 30 mm. In a further aspect, the device has one dimension that is greater than 3 cm, even up to or greater than 10 cm, 20 cm, or even 30 cm.

In a further aspect, described herein is method for preparing a device comprising an agent, comprising
 (a) admixing at least one polymer and at least one agent to produce an admixture;
 (b) processing the admixture to produce a device of a desired shape, wherein the device comprises at least two exposed surfaces; and
 (c) contacting the device with a sufficient amount of a fluid for a sufficient time to change the surface morphology of the polymer, wherein at least one exposed surface or at least one part of at least one exposed surface of the device is not contacted with the fluid, and
wherein steps (a) and (b) do not involve the use of a solvent.

In another aspect, described herein is a method for preparing a device comprising an agent, comprising
 (a) admixing at least one polymer and at least one agent to produce an admixture;
 (b) processing the admixture to produce a device of a desired shape; and
 (c) contacting the device with a sufficient amount of a fluid for a sufficient time to change the surface morphology of the polymer,
wherein steps (a) and (b) do not involve the use of a solvent.

In another aspect, described herein is a method for preparing a device comprising an agent, comprising
 (a) admixing at least one polymer and at least one agent to produce an admixture;
 (b) processing the admixture to produce a device of a desired shape; and
 (c) contacting the device with a sufficient amount of a fluid for a sufficient time to change the surface morphology of the polymer,
wherein steps (a) and (b) involves the use of a non-solvent for the polymer.

In a further aspect, described herein is method for preparing a device comprising at least one polymer and at least one agent, comprising contacting the device with the agent incorporated therein with a sufficient amount of a fluid for a sufficient time to change the surface morphology of the polymer.

In another method, described herein is a method for preparing a device comprising at least one polymer and at least one agent, comprising contacting the device with the agent incorporated therein with a sufficient amount of a fluid for a sufficient time to change the surface morphology of the polymer, wherein at least one exposed surface or at least one part of at least one exposed surface of the device is not contacted with the fluid.

In certain aspects, the polymer and agent are admixed to form a blend or admixture. Admixing step (a) can be performed using techniques known in the art. For example, the polymer and agent can be dry blended (i.e., mixing of particulates of the polymer and the agent) using, for example, a Patterson-Kelley V-blender, or granulated prior to processing step (b). It is contemplated that other components such as, for example, excipients, can be admixed with the polymer and the agent prior to processing.

In certain aspects of the methods described herein, the admixing step does not involve the use of a solvent. There are a number of disadvantages associated with the use of a solvent during the admixing of the polymer and the agent. First, the use of a solvent during admixing requires additional processing steps to remove the solvent. Second, if the delivery system is to be implanted into a subject, the selected solvent has to be biocompatible if any residual solvent remains in the device. The solvent can adversely affect the overall morphology of the delivery system, which can lead to undesirable release patterns. The solvent can adversely affect the stability of the bioactive agent during the manufacturing process. Finally, the solvent level requires control, because it has to be low enough to meet regulatory guidelines.

It is contemplated that steps (a) and/or (b) can be performed in batch or continuously. In another aspect, steps (a) and (b) can employ a non-solvent for the polymer. The phrase "non-solvent for a polymer" is defined herein as any component or compound that can facilitate the mixing of the polymer and the agent, wherein the polymer is substantially insoluble in the component or compound. In a further aspect, the non-solvent is any solvent that dissolves less than 5%, less than 4%, less than 3%, less than 2%, less than 1%, less than 0.75%, less than 0.5%, less than 0.25%, or 0% by weight of the polymer. In a further aspect, admixing step (a) involves the use the use of a non-solvent for the polymer in granulating the polymer and the agent.

The processing of the admixture is performed under conditions such that the agent is intimately mixed or dispersed throughout the polymer. The admixture can be processed by a variety of techniques, such as, for example, melt extruding, injection molding, compression molding, or roller compacting the admixture into a desired shape or structure. Compression manufacturing techniques can include, but are not limited to tabletting. Depending upon processing conditions, the polymer used as a starting material in the admixing step may or may not be the same polymer present in the final device. For example, the polymer during processing may undergo polymerization or depolymerization reactions, which ultimately can produce a different polymer that was used prior to processing. Thus, the term "polymer" as used herein covers the polymers used as starting materials as well as the final polymer present in the device produced by the methods described herein.

The device can have various shapes and sizes depending upon the processing technique that is selected. In a further aspect, the device comprises at least two exposed surfaces. The term "exposed surface" as defined herein is any surface of the device that can be contacted with the fluid. For example, when the device is a cylindrical rod, the device has three exposed surfaces (the two ends and the longitudinal surface). In further aspects, the device has one exposed surface, two exposed surfaces, three exposed surfaces, or greater than three exposed surfaces that have not been contacted with the fluid. This allows for greater controllability of the rate and direction of the release of the agent. The exposed polymer surface not being contacted with the fluid includes the aspects of both (a) controlling the fluid so as not to contact at least one surface of the device during the contacting step or (b) by removing a portion of the treated polymer layer of the treated device to thereby expose uncontacted polymer surface. For aspect (b), for a rod, for example, the entire rod can be fluid treated and then the rod end(s) sliced, cut, sheared, chopped off, or removed in some other manner to expose untreated surface.

In further aspects, the exposed surface or surfaces that have not been contacted with the fluid can be just a portion of the surface, i.e., not the entire surface. That is, in certain aspects, it is not necessary to fluid treat the entire polymer surface, thus, partial surface treatment can be acceptable. For example, when the device is a rod, one entire end surface can be free of contact with the fluid or just part of the one end surface can be free of contact with the fluid. In further aspects, the exposed surface or surfaces that have not been contacted with the fluid can be both one or more entire surfaces and one or more partial surfaces. For example, when the device is a rod, the entire first end surface can be free of fluid contact and part of the surface of the second end can be free of fluid contact.

In a further aspect, the device can be a depot or implant. In a further aspect, the device can be in the shape of a rod, a fiber, a cylinder, a bead, a ribbon, a disc, a wafer, a free-formed shaped solid, or a variety of other shaped solids. In a further aspect, the device is not a sphere such as, for example, a microsphere or microparticle. The device can have any regular or irregular shape and can have any cross section like circular, rectangular, triangular, oval, and the like. In a further aspect, the device comprises a rod comprising two ends and a longitudinal surface, wherein the ends of the rod are not contacted with the surface, and wherein the longitudinal surface is contacted with the fluid.

The delivery systems produced herein can also include a coated article. In a further aspect, described herein is a method for producing a coated article, comprising (a) coating the outer surface of the article with at least one polymer to produce the coated article; and (b) contacting the coated article with a sufficient amount of a fluid to change the surface morphology of at least part of the surface of the polymer.

In this aspect, depending upon the end-use, an agent can be incorporated in the article prior to coating, the agent can be incorporated in the polymer prior to coating the article, or the agent can be incorporated in the article and the polymer coating. It is contemplated that one or more agents can be incorporated in the article and/or the polymer coating. The term "article" is defined herein as any substrate that is capable of being coated with a polymer. In a further aspect, the article to be coated can be a medical device such as, for example, a stent, suture, surgical clip, rod, pin, anchor, mesh, scaffold, tissue-generating scaffold, medical electronic device, a wound dressing, a membrane, an orthopedic device for delivering an antibiotic or growth factor, a device for a dermal application for delivering an anesthetic or growth factor, and the like.

The coating of the article can be accomplished using techniques known in the art. In a further aspect, the coating can be applied by using a solution or dispersion of the polymer. In this aspect, if the agent is not incorporated into the article prior to coating, the agent can be dissolved or dispersed in the polymer solution. In another aspect, the polymer and, optionally, the agent are melt blended then applied to the outer surface of the article. In another aspect, the polymer and, optionally, the agent are prepared as a powder then powder coated on the article. It is also contemplated that all or a portion of the article can be coated with the polymer or polymer and agent.

For the coated article, typically the entire polymer exposed surfaces are contacted with the fluid. However, similar to the device above, partial contacting, i.e., only a portion of the exposed polymer is contacted with the fluid, can be performed or part of the polymer surface is removed to expose untreated surface.

In a further aspect, once the delivery system (i.e. device or coated article) has been produced, it is contacted with a fluid in order to change the surface properties of the device or coated article and, thus, alter the release properties of the device or coated article. In a further aspect, the device or coated article is contacted with a fluid in a sufficient amount for a sufficient time to change the surface morphology of the polymer. Not wishing to be bound by theory, it is believed that the fluid diffuses into the outer layer (a) to lower the Tg of the polymer or (b) to dissolve and/or gel the polymer, so that the polymer molecules rearrange to produce a smooth or smoother surface coating on the device or coated article. This fluid effect results in changing or altering the surface properties on the device or coated article such as, for example, porosity and permeability, which can ultimately reduce the release of the agent incorporated in the device or the coated article. It is also contemplated that all or a portion of the polymer of the device or coated article can be contacted with the fluid.

The fluid used for the surface treatment can include a single fluid or a mixture of two or more fluids in any ratio. In a further aspect, the fluid can be selected based upon the solubility of the polymer to be used. For example, the fluid can be a mixture of liquids, one of which will solubilize the polymer and the other that does not or both will solubilize the polymer. By selecting the fluid system to be used and the duration of the contacting step, it is possible to change the morphology of the polymer and, ultimately, the release pattern of the device. For example, if slower release of the agent from the device is desired, the device can be contacted with the fluid for longer periods of time in order to change the surface morphology of the device to a greater extent.

In a further aspect, the fluid comprises a liquid. Examples of liquids include, but are not limited to, hydrocarbons, halogenated hydrocarbons, ethers, esters, acids, bases, alcohols, ketones, alkanes, aromatics, and the like. In another aspect, the fluid is methylene chloride, chloroform, acetone, anisole, ethyl acetate, methyl acetate, N-methyl-2-pyrrolidone, hexafluoroisopropanol, tetrahydrofuran, dimethylsulfoxide, water, 2-pyrollidone, triethyl citrate, ethyl lactate, propylene carbonate, benzyl alcohol, benzyl benzoate, Miglyol 810, isopropanol, ethanol, super critical carbon dioxide, acetonitrile, water, or a mixture thereof.

In another aspect, the fluid comprises a gas. Compounds that are gaseous at standard temperature and pressure can be used herein as the fluid. In a further aspect, the gas comprises nitrogen, ethylene oxide, a polyfluorochloro compound, water vapor, a vapor of an organic solvent, or a mixture thereof. The device or coated article can be contacted with the gas at operating conditions, such as ambient, elevated, or reduced temperatures, depending upon the composition of the device or coated article and the gas selected.

The delivery system can be exposed to the fluid once or multiple times. In another aspect, after the contacting step, the fluid can optionally be removed from the delivery system. The amount of fluid that is removed from the delivery system in this aspect can vary, and will depend upon the desired release profile to be achieved. The device or coated article can be contacted with the fluid using techniques known in the art. In a further aspect, when the fluid is a liquid, the device or article can be contacted with the liquid by immersing the device in the liquid or spraying the liquid on the device. In another aspect, during the processing of the polymer/agent admixture, the admixture can be extruded with the fluid. In a further aspect, the polymer/agent admixture can be extruded through a liquid rich dye. In another aspect, the contacting step can be continuous, where a steady stream of fluid is in contact with the device. In other aspects, when the fluid is a liquid, the contacting step can be performed by an annular ring with an aerosol solvent, a pan coating, or by vapor phase equilibration. When the fluid is a gas, in a further aspect, the device or coated article can be contacted with a steady stream of the gas. Alternatively, the device or coated article can be placed in a chamber that is to be filled with the gas. In further aspects, an entire exposed surface or a portion of the exposed surface of the polymer of the delivery systems (devices and coated articles) can be fluid treated. That is, it is not necessary in certain aspects to treat the entire polymer surface.

The time of the fluid exposure can vary depending upon the fluid and polymer selected and the desired release pattern to be achieved. The contacting step can range from greater than zero, such as just over a second, to minutes, to hours, or to several days. In various aspects, the contacting time is from 0.1 seconds to one hour, 0.5 seconds to 30 minutes, one second to 10 minutes, two seconds to 5 minutes, three seconds to 60 seconds, or five seconds to 30 seconds. In another aspect, the contacting time is from one second to 10 seconds or one second to five seconds. In further aspects, different fluids or different mixtures of fluids can be used during a series of fluid exposures.

Other process conditions can include, but are not limited to, temperature and pressure. In a further aspect, when the fluid is a liquid, the temperature of the contacting step is less than the boiling point of the liquid. In another aspect, the temperature of the contacting step is less than the melting point of the polymer. In another aspect, when the fluid is a gas, the pressure of the contacting step can be at atmospheric pressure or greater than atmospheric pressure.

Typically, after the contacting step the delivery system is dried to remove some or all of the fluid. In a further aspect, after the contacting step, the delivery system is washed with water.

In a further aspect, the device is prepared by dry blending a bioactive agent with a poly(lactide-co-glycolide) polymer (PLG) such as, for example, 85:15 PLG. In a further aspect, when the delivery system is a device, the device is prepared by dry blending poly(lactide-co-glycolide), poly(lactide), or a combination thereof, with a bioactive agent to produce an admixture, melt extruding the admixture to produce a rod, contacting the rod with ethyl acetate, and cutting the rod into one or more smaller rods having a predetermined length. In this aspect, the two ends of the cut up rods have not been contacted with the fluid. Thus, the surface morphology of the ends of the rod is different when compared to longitudinal surface of the rod.

A variety of agents can be used in the methods described herein. As used herein, in reference to the invention, "agent" includes both a bioactive agent or a non-bioactive agent.

In a further aspect, the agent is a bioactive agent. The term "bioactive agent" (i.e., biologically active agent, drug, or medicament) as used herein includes without limitation physiologically or pharmacologically active substances that act locally or systemically in the body. A biologically active agent is a substance used for the treatment, prevention, diagnosis, cure or mitigation of disease or illness, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Various forms of the medicaments or biologically active materials can be used, which are capable of being released from the solid matrix into adjacent tissues or fluids. A liquid or solid bioactive agent can be incorporated in the delivery systems described herein. The bioactive agents are at least very slightly water soluble, preferably moderately water soluble, and are diffusible through the polymeric composition. They can be acidic, basic, or amphoteric salts. They can be nonionic molecules, polar molecules, or molecular complexes capable of hydrogen bonding. The biologically-active agent may be included in the compositions in the form of, for example, an uncharged molecule, a molecular complex, a salt, an ether, an ester, an amide, polymer drug conjugate, or other form to provide the effective biological or physiological activity. Examples of bioactive agents that incorporated into systems herein include, but are not limited to, peptides, proteins such as hormones, enzymes, antibodies and the like, nucleic acids such as aptamers, iRNA, DNA, RNA, antisense nucleic acid or the like, antisense nucleic acid analogs or the like, low-molecular weight compounds, or high-molecular-weight compounds. Bioactive agents contemplated for use in the delivery systems include anabolic agents, antacids, anti-asthmatic agents, anti-cholesterolemic and anti-lipid agents, anticoagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, antispasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and antithyroid agents, tissue growth agents, uterine relaxants, vitamins, or antigenic materials. Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines. Representative drugs or bioactive materials that can be used in the polymer system or solid matrix of the present invention include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent may further be a substance capable of acting as a stimulant, sedative, hypnotic, analgesic, anticonvulsant, and the like. The delivery system can contain a large number of bioactive active agents either singly or in combination. Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anti-convulsants such as phenytoin sodium, diazepam, and the like; antidepressants such as isocarboxazid, amoxapine, and the like;antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxam®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; antimalarials, L-dopa, diuretics such as furosemide, spironolactone, and the like; antiulcer drugs such as rantidine HCl, cimetidine HCl, and the like.

Immunological agents that can be used herein include, cytokines, interleukins, interferon, colony stimulating factor, tumor necrosis factor, and the like; allergens such as cat dander, birch pollen, house dust mite, grass pollen, and the like; antigens of cush bacterial organisms as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni,* and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia rickettsii, Rickettsia typhi, Mycoplasma pneumoniae, Chlamyda psittaci, Chlamydia trachomatis, Plasmodium falciparum, Trypanasoma brucei,*

*Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a specific aspect, the bioactive agent comprises a drug, an immunological agent, an antigen, a protein, a peptide, an oligonucleotide, or a mixture thereof.

Although there are numerous applications for bioactive agents, the devices and coated articles produced herein are useful in releasing non-bioactive agents as well. Examples of non-bioactive agents include, but are not limited to, an adhesive, a pesticide, a fragrance, an antifoulant, a dye, a salt, an oil, an ink, a cosmetic, a catalyst, a detergent, a curing agent, a flavor, a fuel, a herbicide, a metal, a paint, a photographic agent, a biocide, a pigment, a plasticizer, a propellant, a stabilizer, a polymer additive, or any combination thereof.

The polymers useful herein are biocompatible and either biodegradable or non-biodegradeable. In a further aspect, polymers useful in the methods described herein include, but are not limited to, a silicone, a poly(diene) such as poly(butadiene) and the like; a poly(alkene) such as polyethylene, polypropylene, and the like; a poly(acrylic) such as poly(acrylic acid) and the like; a poly(methacrylic) such as poly(methyl methacrylate) or a poly(hydroxyethyl methacrylate), and the like; a poly(vinyl ether); a poly(vinyl alcohol); a poly(vinyl ketone); a poly(vinyl halide) such as poly(vinyl chloride) and the like; a poly(vinyl nitrile), a poly(vinyl ester) such as poly(vinyl acetate) and the like; a poly(vinyl pyridine) such as poly(2-vinyl pyridine) or poly(5-methyl-2-vinyl pyridine) and the like; a poly(styrene); a poly(carbonate); a poly(ester); a poly(orthoester) including a copolymer; a poly(esteramide); a poly(anhydride); a poly(urethane); a poly(amide); a cellulose ether such as methyl cellulose, hydroxyethyl cellulose, hydroxypropyl methyl cellulose, and the like; a cellulose ester such as cellulose acetate, cellulose acetate phthalate, cellulose acetate butyrate, and the like; a poly(saccharide), a protein, gelatin, starch, gum, a resin, and the like. These materials may be used alone, as physical mixtures (blends), combinations, or as copolymers. Derivatives of any of the polymers listed above can also be used.

In a specific aspect, the polymer comprises a silicone, a poly(diene), a poly(alkene), a poly(acrylic), a poly(methacrylic), poly(vinyl ether), a poly(vinyl alcohol), a poly(vinyl ketone), a poly(vinyl halide), a poly(vinyl nitrile), a poly(vinyl ester), a poly(vinyl pyridine), a poly(styrene), a poly(carbonate), a poly(ester), a poly(orthoester), a poly(esteramide), a poly(anhydride), a poly(urethane), a poly(amide), a cellulose ether, a cellulose ester, a poly(saccharide), a protein, gelatin, starch, a gum, a resin, or any combination, blend, or copolymer thereof.

In a further aspect, the polymer of the device or coated article includes a biocompatible, non-biodegradable polymer such as, for example, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend, combination, or copolymer thereof.

In another aspect, the polymer of the device or coated article includes a biocompatible, biodegradable polymer such as, but limited to, a poly(lactide), a poly(glycolide), a poly(lactide-co-glycolide), a poly(lactic acid), a poly(glycolic acid), a poly(lactic acid-co-glycolic acid), a poly(caprolactone), a poly(orthoester), a poly(phosphazene), a poly(hydroxybutyrate) or a copolymer containing a poly(hydroxybutarate); a poly(lactide-co-caprolactone); a polycarbonate; a polyesteramide; a polyanhydride; a poly(dioxanone), a poly(alkylene alkylate); a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

In another aspect, the polymer comprises a biodegradable polymer, wherein the biodegradable polymer comprises a poly(caprolactone), a poly(orthoester), a poly(phosphazene), a poly(hydroxybutyrate) or a copolymer containing poly(hydroxybutarate), a poly(lactide-co-caprolactone), a polycarbonate, a polyesteramide, a polyanhydride, a poly(dioxanone), a poly(alkylene alkylate), a copolymer of polyethylene glycol and polyorthoester, a biodegradable polyurethane, a poly(amino acid), a polyetherester, a polyacetal, a polycyanoacrylate, poly(oxyethylene)/poly(oxypropylene) copolymer, or a combination, blend, or copolymer thereof.

In a further aspect, the device is an implant or rod comprising a biodegradable polymer, wherein the bioactive agent is imbedded within the implant. In a further aspect, the bioactive agent is encapsulated in an implant or rod composed of poly(lactide-co-glycolide), poly(lactide), poly(glycolide), or a mixture thereof. Lactide/glycolide polymers for drug-delivery formulations are typically made by melt polymerization through the ring opening of lactide and glycolide monomers. Some polymers are available with or without carboxylic acid end groups. When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group. The biodegradable polymers herein can be blocked or unblocked. In a further aspect, linear lactide/glycolide polymers are used; however star polymers can be used as well. In certain aspects, high molecular weight polymers can be used for medical devices, for example, to meet strength requirements. In other aspects, low or medium molecular weight polymers can be used for drug-delivery and vaccine delivery products where resorption time of the polymer and not material strength is as important. The lactide portion of the polymer has an asymmetric carbon. Commercially racemic DL-, L-, and D-polymers are available. The L-polymers are more crystalline and resorb slower than DL-polymers. In addition to copolymers comprising glycolide and DL-lactide or L-lactide, copolymers of L-lactide and DL-lactide are available. Additionally, homopolymers of lactide or glycolide are available.

In the case when the biodegradable polymer is poly(lactide-co-glycolide), poly(lactide), or poly(glycolide), the amount of lactide and glycolide in the polymer can vary. In a further aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide) where the ratios are mole ratios.

Polymers that are useful for the present invention are those having an intrinsic viscosity of from 0.15 to 2.0, 0.15 to 1.5 dL/g, 0.25 to 1.5 dL/g, 0.25 to 1.0 dL/g, 0.25 to 0.8 dL/g, 0.25 to 0.6 dL/g, or 0.25 to 0.4 dL/g as measured in chloroform at a concentration of 0.5 g/dL at 30° C. In a further aspect, when the biodegradable polymer is poly(lactide-co-glycolide), poly(lactide), or poly(glycolide), the polymer has an intrinsic viscosity of from 0.15 to 2.0, 0.15 to 1.5 dL/g, 0.25 to 1.5 dL/g, 0.25 to 1.0 dL/g, 0.25 to 0.8 dL/g, 0.25 to 0.6 dL/g, or 0.25 to 0.4 dL/g as measured in chloroform at a concentration of 0.5 g/dL at 30° C.

When the device or coated article is used to deliver a bioactive agent, other pharmaceutically-acceptable components can be incorporated in the delivery system in combination with the bioactive agent. For example, the pharmaceutically-acceptable component can include, but is not limited to, a fatty acid, a sugar, a salt, a water-soluble polymer such as polyethylene glycol, a protein, polysacharride, or carboxmethyl cellulose, a surfactant, a plasticizer, a high- or low-molecular-weight porosigen such as polymer or a salt or sugar, or a hydrophobic low-molecular-weight compound such as cholesterol or a wax.

In further aspects of the invention, the invention includes devices and coated articles made by the methods described herein.

In a further aspect, described herein are devices comprising at least one polymer and at least one agent, wherein the agent is dispersed in the polymer, wherein the device comprises at least two exposed surfaces of the same polymer, wherein at least one of the exposed surfaces or at least one part of at least one exposed surface has surface morphology different than the other exposed surface or surfaces. The device can be composed of one polymer or a mixture of two or more polymers. Regardless if one or more polymers are used, the polymer or polymers are evenly distributed throughout the device. Thus, in various aspects, when two or more polymers are used to produce the device, the polymers are not two distinct polymer phases (e.g., co-extrusion of two polymers) but a mixture of the polymers.

Using the techniques described herein, it is possible to change the surface morphology of one or more exposed surfaces of the delivery system so that the delivery system has varying (i.e., different) surface morphologies. This is desirable for a number of different applications. For example, when the delivery system is a rod used as an implant, wherein the ends of the rod are not contacted with a fluid but the longitudinal surface is contacted with the fluid, the longitudinal surface has a surface morphology that is different than that of the ends of the rod. In this aspect, the rate of release and the direction of release can be better controlled. The delivery systems produced by the methods described herein also have the added benefit of containing more of the agent (i.e., higher loading). In a further aspect, the agent is greater than 30%, greater than 40%, or greater than 50% by weight of the device or coating on the coated article. In the case when the delivery system is to be implanted into a subject, the greater loading capacity results in higher doses of the agent that can released over a longer period of time as well as the use of smaller implants.

In another aspect, described herein is a polymer coated article that has been treated with a fluid of this invention. In a specific aspect, the article comprises at least one first exposed surface and a polymer coating comprising a second exposed surface, wherein the polymer coating is connected to the first exposed surface of the article, wherein the morphology near the second exposed surface of at least part of the polymer coating is different than the morphology of the remaining polymer coating. The term "connected" as used herein includes when the polymer is adjacent to (i.e., intimate contact with) the article or is indirectly attached to the article by way of one or more intermediate layers. As described above, the agent can be present in the article prior to the application of the polymer coating, the agent can be incorporated into the polymer prior to coating, or a combination thereof. The morphology near the second exposed surface of at least part of the polymer coating is different than the morphology of the remaining polymer coating. The term "near" is defined herein to include the exposed surface of the polymer coating and a predetermined distance below the exposed surface of the coating. The distance below the surface can vary and will depend upon the selection of the fluid, the contacting time with the fluid, and the desired release pattern. At least part of or the entire polymer surface can be fluid treated, and thus have a different morphology than the underlying polymer surface.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in degrees Centigrade (° C.) or is at ambient temperature, and pressure is at or near atmospheric. There are numerous variations and combinations of reaction conditions, e.g., component concentrations, component mixtures, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Fabrication of Implants Containing 45 wt % Vitamin $B_{12}$

An implant formulation was made with vitamin $B_{12}$ and poly(DL-lactide). The poly(DL-lactide) was ester capped and had an inherent viscosity of 0.37 dL/g. The inherent viscosity was measured at 30° C. with 0.5 gm/dL polymer concentration in chloroform.

The desired vitamin $B_{12}$ content in the implant was 45 wt % vitamin $B_{12}$. First vitamin $B_{12}$ (2.25 gm) and the poly(DL-lactide) (2.75 gm) were dry blended using a mortar and pestle to form a blended powder. Next a Tinius Olsen Model UE-4-78 melt plastometer was used to extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 1.5-mm die was used, meaning that the core of the die was 1.5 mm in diameter. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. The blend, approximately 5 gm, was loaded into the Tinius Olsen which had been equilibrated to 90° C. A charging rod was placed in the core of the Tinius Olsen to compress the blend and a weight of 3.7 kg was placed on the end of the charging rod to aid in the compaction of the blend. The equilibration time for the blend to melt lasted for about 15 minutes. After an extrusion load of 10,400 gm was placed on the charging rod, the plug was removed from the discharge area to begin the extrusion run. The 5-gm charge afforded 5 segments of extruded rod each having a length of about 20 cm.

Next ethyl acetate was placed in a graduated cylinder and one end of the rod was held with forceps and dipped in the ethyl acetate for about 5 seconds. The implants were then dried at ambient temperature. Once the implants were dry, the ends of the extruded rod segments were cut and discarded. The remaining treated segment was cut into implants that had the cylindrical portion treated with ethyl acetate and the ends left untreated. The only treated part was thus that portion of the implant that came into contact with the cylindrical wall of the implant. The vitamin $B_{12}$ content was 45 wt %. The in vitro release characteristics of the vitamin $B_{12}$ implants made with poly(DL-lactide) by the above-described manufacturing process (with and without ethyl acetate exposure) are shown in FIG. 1. These release data showed that the ethyl acetate treated implants released vitamin $B_{12}$ with less burst of vitamin $B_{12}$ and at a slower rate of release as compared to implants not treated with ethyl acetate.

Example 2

Fabrication of Implants Containing 30 wt % of leuprolide a 9-Amino-Acid Peptide (PROPHETIC)

An implant formulation can be made with small peptides (3 to 12 amino acids) or large peptides (13 to 50 amino acids ) with poly(DL-lactide) or poly(lactide-co-glycolide).

Leuprolide is a 9-amino-acid peptide that is an LHRH agonist indicated for the treatment of prostate cancer. The desired leuprolide content in the implant is 35 wt % peptide. To prepare a depot formulation of luprolide, leuprolide and poly(DL-lactide) or poly(lactide-co-glycolide) can be dry blended in a variety of ways including the use of a mortar and pestle to form a blended powder. Next this blend or admixture is added to a twin-screw extruder having a 2-mm die. An extruded rod of is then made. The rod is subsequently cut to form implants. Each implant is dipped in ethyl acetate for about one time for about 5 seconds. The implants are then dried at ambient temperature.

Example 3

Fabrication of Implants Containing 10 wt % of Octreotide a 14-Amino-Acid Peptide (PROPHETIC)

An implant formulation can be made with small peptides (3 to 12 amino acids) or large peptides (13 to 50 amino acids ) with poly(DL-lactide) or poly(lactide-co-glycolide).

Octreotide is a 14-amino-acid peptide indicated for the treatment of agromegaly. The desired octreotide content in the implant is 10 wt % peptide. To prepare a depot formulation of octreotide, octreotide and poly(DL-lactide) or poly (lactide-co-glycolide) can be dry blended in a variety of ways including the use of a mortar/pestle or by mixing preformed polymer and peptide particles in a V-blender to form a blended powder. Next this blend or admixture is added to a twin-screw extruder having a 2-mm die. An extruded rod of is then made. The rod is subsequently cut to form implants. Each implant is dipped in ethyl acetate for about one time for about 5 seconds or can be dipped for 2 seconds for three times. The implants are then dried at ambient temperature.

Example 4

Fabrication of Implants Containing 44 wt % Deslorelin

An implant formulation was made with Deslorelin and poly(DL-lactide). The poly(DL-lactide) was ester capped and had an inherent viscosity of 0.37 dL/g. The inherent viscosity was measured at 30° C. with 0.5 gm/dL polymer concentration in chloroform.

The desired Deslorelin content in the implant was 44 wt % Deslorelin. First Deslorelin (1.6 gm) and the poly(DL-lactide) (1.6 gm) were dry blended using a mortar and pestle to form a blended powder. Next a Tinius Olsen Model UE-4-78 melt plastometer was used to extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 3.9-mm die was used, meaning that the core of the die was 3.9 mm in diameter. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. The blend, approximately 3.2 gm, was loaded into the Tinius Olsen which had been equilibrated to 90° C. A charging rod was placed in the core of the Tinius Olsen to compress the blend and a weight of 6.6 kg was placed on the end of the charging rod to aid in the compaction of the blend. The equilibration time for the blend to melt lasted for about 15 minutes. After an extrusion load of 10,400 gm was placed on the charging rod, the plug was removed from the discharge area to begin the extrusion run. The 3.2-gm charge afforded 3 segments of extruded rod each having a length of about 20 cm.

The batch was then segregated into four sections. The first section was not surface treated. The second was treated with ethyl acetate. The third was treated with methylene chloride. The fourth was treated with acetone.

Figure 2:
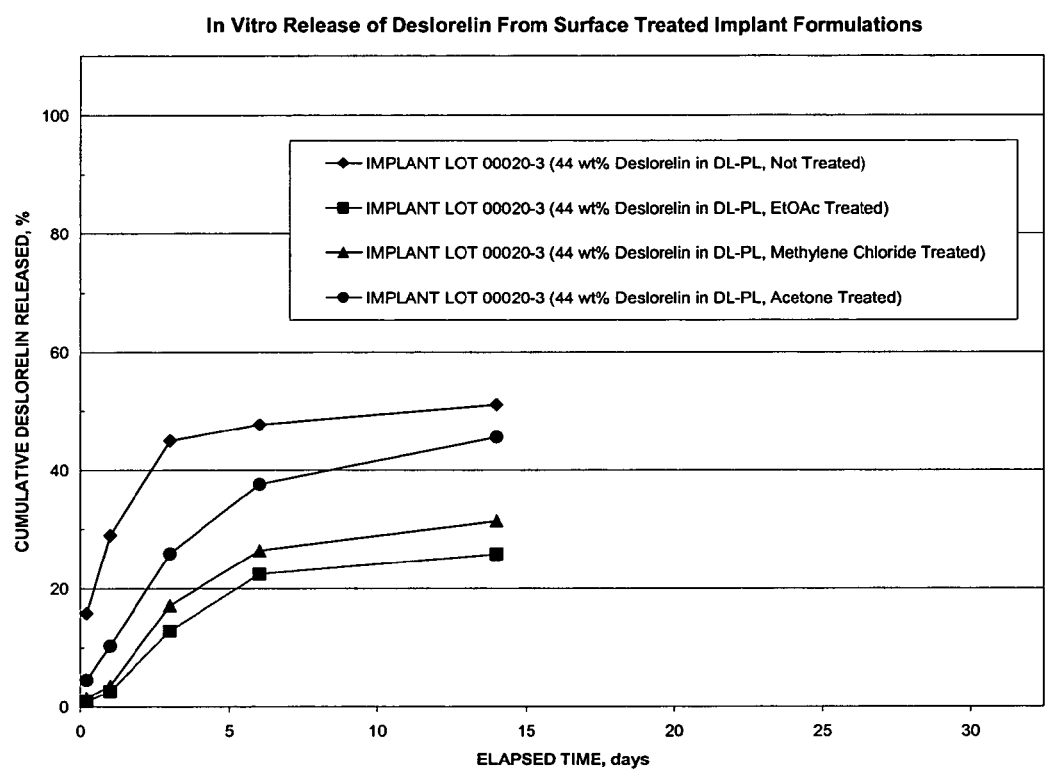
FIG. 2 shows the in vitro release characteristics of Deslorelin implants (44 wt %) made with poly(DL-lactide) with and without fluid exposure.

The second section was cut into implants approximately 4 mm in length. The entire implant was then surface treated with ethyl acetate by first mounting the implant on a needle and then dipping into a vial of ethyl acetate. Rod sections three and four were likewise handled, treating their respective surfaces with methylene chloride and acetone. The implants were then dried at ambient temperature. The Deslorelin content was 44 wt %. The in vitro release characteristics of the Deslorelin implants made with poly(DL-lactide) by the above-described manufacturing process (with and without solvent exposure) are shown in FIG. 2. These release data showed that the solvent treated implants released Deslorelin with less burst of Deslorelin (10-33% of the non-treated formulation) and at a slower rate of release as compared to implants not treated with solvent.

Example 5

Fabrication of Implants Containing 50 wt % Risperidone

An implant formulation was made with Risperidone and poly(DL-lactide). The poly(DL-lactide) was ester capped and had an inherent viscosity of 0.37 dL/g. The inherent viscosity was measured at 30° C. with 0.5 gm/dL polymer concentration in chloroform.

The desired Risperidone content in the implant was 50 wt % Risperidone. First Risperidone (2.0 gm) and the poly(DL-lactide) (2.0 gm) were dry blended using a mortar and pestle to form a blended powder. Next a Tinius Olsen Model UE-4-78 melt plastometer was used to extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 3.9-mm die was used, meaning that the core of the die was 3.9 mm in diameter. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. The blend, approximately 4 grams, was loaded into the Tinius Olsen which had been equilibrated to 90° C. A charging rod was placed in the core of the Tinius Olsen to compress the blend and a weight of 6.6 kg was placed on the end of the charging rod to aid in the compaction of the blend. The equilibration time for the blend to melt lasted for about 20 minutes. After an extrusion load of 10,400 grams was placed on the charging rod, the plug was removed from the discharge area to begin the extrusion run. The 3.2-gm charge afforded 4 segments of extruded rod each having a length of about 20 cm.

The batch was then segregated into three sections. The first section was not surface treated. The second was treated with ethyl acetate. The third was treated with ethanol.

Figure 3:
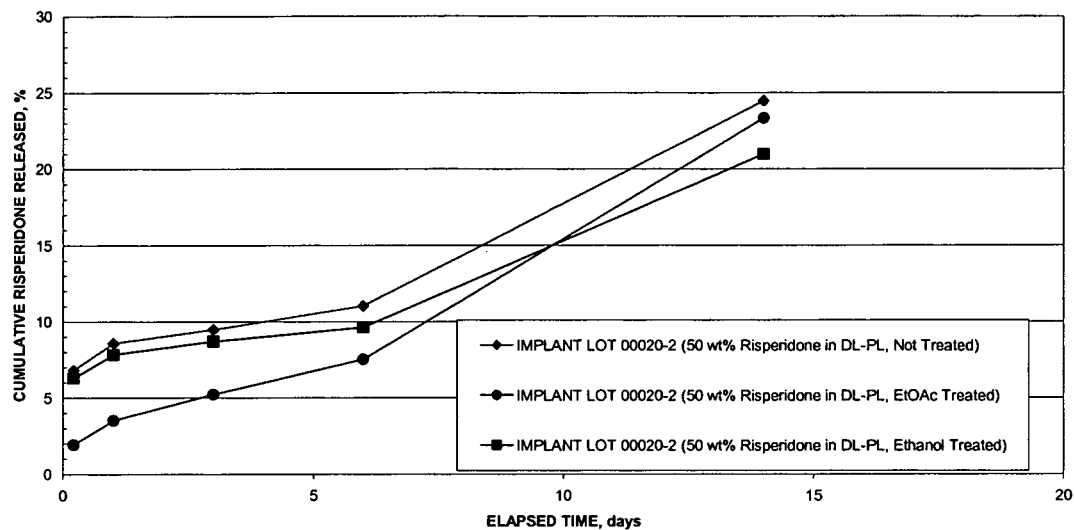
FIG. 3 shows the in vitro release characteristics of Risperidone implants (50 wt %) made with poly(DL-lactide) with and without fluid exposure.

The second section was cut into implants approximately 4 mm in length. The entire implant was then surface treated with ethyl acetate by first mounting the implant on a needle and then dipping into a vial of ethyl acetate. The third rod section was likewise handled, with its surface treated with ethanol. The implants were then dried at ambient temperature. The Risperidone content was 50 wt %. The in vitro release characteristics of the Risperidone implants made with poly(DL-lactide) by the above-described manufacturing process (with and without solvent exposure) are shown in FIG. 3. These release data showed that the solvent treated implants released Risperidone with less burst of Risperidone (<30% of the non-treated formulation for ethyl acetate) and at a slower rate of release as compared to implants not treated with solvent. In particular the reduction of cumulative release in implants treated with ethanol increased over time from a less than 8% reduction at burst to a greater than 14% reduction at Day 14.

Example 6

Fabrication of Implants Containing 50 wt % Vitamin $B_{12}$

An implant formulation was made with vitamin $B_{12}$ and poly(DL-lactide). The poly(DL-lactide) was ester capped and had an inherent viscosity of 0.37 dL/g. The inherent viscosity was measured at 30° C. with 0.5 gm/dL polymer concentration in chloroform.

The desired vitamin $B_{12}$ content in the implant was 50 wt % vitamin $B_{12}$. First vitamin $B_{12}$ (2 gm) and the poly(DL-lactide) (2 gm) were dry blended using a mortar and pestle to form a blended powder. Next a Tinius Olsen Model UE-4-78 melt plastometer was used to extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 3.9-mm die was used, meaning that the core of the die was 3.9 mm in diameter. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. The blend, approximately 4 grams, was loaded into the Tinius Olsen which had been equilibrated to 90° C. A charging rod was placed in the core of the Tinius Olsen to compress the blend and a weight of 6.6 kg was placed on the end of the charging rod to aid in the compaction of the blend. The equilibration time for the blend to melt lasted for about 20 minutes. After an extrusion load of 15,245 gm was placed on the charging rod, the plug was removed from the discharge area to begin the extrusion run. The 4-gm charge afforded 4 segments of extruded rod each having a length of about 20 cm.

The batch was then segregated into four sections. The first section was not surface treated. The second was treated with ethyl acetate. The third was treated with methylene chloride. The fourth was treated with acetone.

Figure 4:
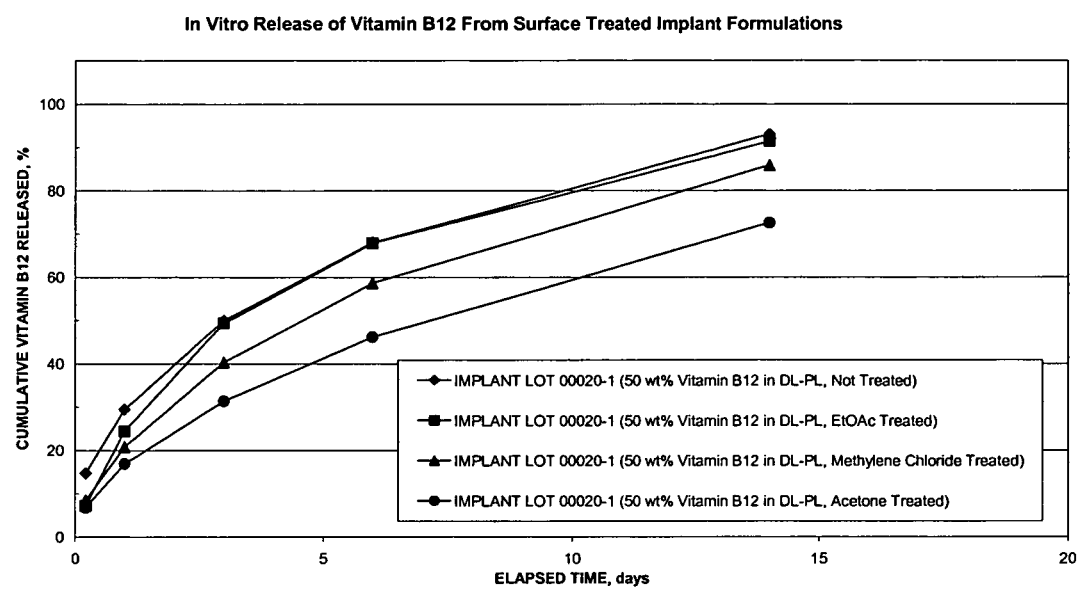
FIG. 4 shows the in vitro release of vitamin $B_{12}$ (50 wt %) from poly(DL-lactide) implants with and without fluid exposure.

The second section was cut into implants approximately 4 mm in length. The entire implant was then surface treated with ethyl acetate by first mounting the implant on a needle and then dipping into a vial of ethyl acetate. Rod sections three and four were likewise handled, treating their respective surfaces with methylene chloride and acetone. The implants were then dried at ambient temperature. The vitamin $B_{12}$ content was 50 wt %. The in vitro release characteristics of the vitamin $B_{12}$ implants made with poly(DL-lactide) by the above-described manufacturing process (with and without solvent exposure) are shown in FIG. 4. The release data clearly shows a marked reduction of the burst associated with the non-treated implants when using any of the three solvents. The smallest burst reduction is 42.6% and the largest is 54.1%. The most dramatic results are seen in this formulation with the use of acetone as the solvent.

Example 7

Fabrication of Implants Containing 45 wt % Vitamin $B_{12}$

An implant formulation was made with vitamin $B_{12}$ and EVA (ethyl vinyl acetate). The desired vitamin $B_{12}$ content in the implant was 45 wt % vitamin $B_{12}$. First vitamin $B_{12}$ (2 gm) and the EVA (2 gm) were dry blended using a mortar and pestle to form a blended powder. Next a Tinius Olsen Model UE-4-78 melt plastometer was used to extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 3.9-mm die was used, meaning that the core of the die was 3.9 mm in diameter. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. The blend, approximately 4 grams, was loaded into the Tinius Olsen which had been equilibrated to 90° C. A charging rod was placed in the core of the Tinius Olsen to compress the blend and a weight of 6.6 kg was placed on the end of the charging rod to aid in the compaction of the blend. The equilibration time for the blend to melt lasted for about 20 minutes. After an extrusion load of 15,245 grams was placed on the charging rod, the plug was removed from the discharge area to begin the extrusion run. The 4-gm charge afforded 4 segments of extruded rod each having a length of about 20 cm.

The batch was then segregated into three sections. The first section was not surface treated. The second was treated with methylene chloride for 10 seconds. The third was treated with methylene chloride for 60 seconds.

Figure 5:
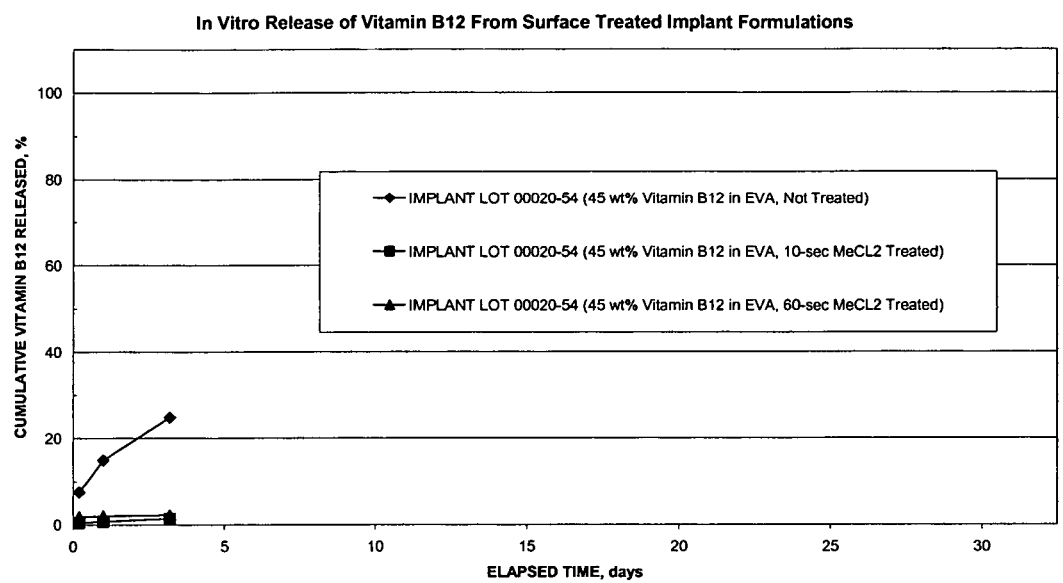
FIG. 5 shows the in vitro release of vitamin $B_{12}$ (45 wt %) from ethyl vinyl acetate implants with and without fluid exposure.

The second section was cut into implants approximately 4 mm in length. The entire implant was then surface treated with methylene chloride by first mounting the implant on a needle and then dipping into a vial of methylene chloride for 10 seconds. Rod section three was likewise handled, treating the surface with methylene chloride for 60 seconds. The implants were then dried at ambient temperature. The vitamin $B_{12}$ content was 45 wt %. The in vitro release characteristics of the vitamin $B_{12}$ implants made with EVA by the above-described manufacturing process (with and without solvent exposure) are shown in FIG. 5. The release data clearly shows a drastic reduction of the burst and the release of the vitamin $B_{12}$ from the implants treated with methylene chloride.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for preparing a device comprising an agent, comprising
   (a) admixing at least one polymer and at least one agent to produce an admixture;
   (b) processing the admixture to produce a device of a desired shape, wherein the device comprises at least two exposed surfaces; and
   (c) contacting the device with a sufficient amount of a fluid for a sufficient time to change the surface morphology of the polymer; wherein the fluid diffuses into the outer layer of the polymer to gel the polymer thereby producing a smoother surface coating on the device, wherein at least one exposed surface or least one part of at least one exposed surface of the device is not contacted with the fluid;
   wherein steps (a) and (b) do not involve the use of a solvent; and
   wherein the fluid consists essentially of methylene chloride, chloroform, acetone, anisole, methyl acetate, ethyl acetate, N-methyl-2- pyrrolidone, hexafluoroisopropanol, tetrahydrofuran, dimethylsulfoxide, 2-pyrollidone, triethyl citrate, ethyl lactate, propylene carbonate, benzyl alcohol, benzyl benzoate, Miglyol 810, isopropanol, ethanol, super critical carbon dioxide, or acetonitrile, or a mixture thereof.

2. The method of claim 1, wherein at least two exposed surfaces of the device are not contacted with the fluid.

3. The method of claim 1, wherein two exposed surfaces of the device are not contacted with the fluid.

4. The method of claim 1, wherein the device comprises a rod, a fiber, a disc, a wafer, a bead, a ribbon, or a cylinder.

5. The method of claim 1, wherein the device comprises a rod comprising two ends and a longitudinal surface, wherein the ends of the rod are not contacted with the fluid, and wherein the longitudinal surface is contacted with the fluid.

6. The method of claim 1, wherein the device comprises a rod comprising two ends and a longitudinal surface, wherein after contacting the device with the fluid, at least one end of the rod is removed to expose an untreated end.

7. The method of claim 1, wherein the processing step comprises melt extruding, injection molding, compression molding, or roller compacting the admixture into a desired shape.

8. The method of claim 1, wherein the fluid consists essentially of ethyl acetate.

9. The method of claim 1, wherein the agent comprises a bioactive agent.

10. The method of claim 9, wherein the bioactive agent comprises a drug, an immunological agent, an antigen, a protein, a peptide, an oligonucleotide, or a mixture thereof.

11. The method of claim 1, wherein the agent comprises an adhesive, a pesticide, a fragrance, an antifoulant, a dye, a salt, an oil, an ink, a cosmetic, a catalyst, a detergent, a curing agent, a flavor, a fuel, a herbicide, a metal, a paint, a photographic agent, a biocide, a pigment, a plasticizer, a propellant, a stabilizer, or a polymer additive, or any combination thereof.

12. The method of claim 1, wherein the polymer comprises a biodegradable polymer, wherein the biodegradable polymer comprises a poly(lactide), a poly(glycolide), a poly(lactide-co-glycolide), a poly(lactic acid), a poly(glycolic acid), a poly(lactic acid-co-glycolic acid), a poly(caprolactone), or a poly(lactide-co-caprolactone), or a combination, blend, or copolymer thereof.

13. The method of claim 12, wherein the biodegradable polymer comprises a polymer formed from components comprising 40 to 100 mole % lactide and from 0 to 60 mole % glycolide.

14. The method of claim 12, wherein the biodegradable polymer comprises poly(lactide-co-glycolide), poly(lactide), poly(caprolactone), or a combination, blend, or copolymer thereof.

15. The method of claim 1, wherein admixing step (a) comprises dry blending poly(lactide-co-glycolide), poly(lactide), or a combination, blend, or copolymer thereof, with a bioactive agent to produce an admixture, melt extruding the admixture to produce a rod, contacting the rod with ethyl acetate, and cutting the rod into one or more smaller rods having a predetermined length.

16. The method of claim 1, wherein the device is not a sphere.

17. The method of claim 1, wherein the device is not a microsphere or a microparticle.

18. The method of claim 1, wherein the polymer comprises a polymer of ethylene-vinyl acetate.

* * * * *